United States Patent [19]
Mehrotra et al.

[11] Patent Number: 6,136,316
[45] Date of Patent: Oct. 24, 2000

[54] HEPATOPROTECTIVE COMPOSITIONS AND COMPOSITION FOR TREATMENT OF CONDITIONS RELATED TO HEPATITIS B AND E INFECTION

[75] Inventors: Raj Mehrotra, Lucknow; Chandra Kant Katiyar; Ajaya Prakash Gupta, both of Ghaziabad, all of India

[73] Assignee: Dabur Research Foundation, Ghaziabad, India

[21] Appl. No.: 08/843,709

[22] Filed: Apr. 16, 1997

[30] Foreign Application Priority Data

Apr. 17, 1996 [IN] India ................................ 823/DEL/96
Feb. 25, 1997 [IN] India ................................ 484/DEL/97

[51] Int. Cl.[7] ............................ A61K 35/78; A61K 9/20; A61K 9/48
[52] U.S. Cl. ...................... 424/195.1; 424/439; 424/451; 424/464; 424/489; 514/893; 514/894; 514/962
[58] Field of Search ................................ 424/195.1, 439, 424/451, 464, 489; 514/893, 894, 962

[56] References Cited

U.S. PATENT DOCUMENTS 5,145,955  9/1992  Aswal et al. ............................ 536/124
5,411,733  5/1995  Hozumi et al. ........................ 424/195.1
5,466,455  11/1995 Huffstutler, Jr. et al. ........... 424/195.1

OTHER PUBLICATIONS

Mowrey, D.B., in The Scientific Validation of Herbal Medicine, Keats Publishing, Inc., New Canaan, CT, p. 171, 1986.
The Merck Manual of Diagnosis and Therapy, Sixteenth Edition, Merck & Co., Inc., Rahway, NJ, pp. 897–904, 1992.

*Primary Examiner*—Michael G. Wityshyn
*Assistant Examiner*—Janet M. Kerr
*Attorney, Agent, or Firm*—Ladas & Parry

[57] ABSTRACT

The invention provides a novel polyherbal composition useful for treating acute Hepatitis E virus infection including acute liver failure due to HEV infection, healthy Hepatitis B virus carriers who develop superadded hepatitis E virus infection, acute hepatitis B virus infection, and animal hepadna virus, therapeutic effects on hepatitis B virus infection and also used as a hepatoprotective agent, said composition comprising essentially extracts of plants *Rheum emodi* Wall., *Phyllanthus amarus* Linn., *Eclipta alba* Hassk., *Andrographis paniculate* Nees., and *Picrorhiza kurroa* Royle ex Benth., and optionally *Fumaria officinalis, Tinospora cordifolia* Miers., *Terminalia chebula* Retz., *Cichorium intybus* Linn., *Tephrosea purpurea* Linn. and *Boerhaavia diffusa* Linn.

9 Claims, 20 Drawing Sheets

(15 of 20 Drawing Sheet(s) Filed in Color)

REVAND CHINI (RHEUM EMODI)

PHOTOGRAPH OF THIN LAYER CHROMATOGRAM (TLC)
( DETECTION UNDER UV-at 254 nm)

REVAND CHINI (RHEUM EMODI)

PHOTOGRAPH OF THIN LAYER CHROMATOGRAM (TLC)
( DETECTION UNDER UV-at 366 nm)

BHUMYAMLALAKI (PHYLLANTHUS NIRURI/AUREUS)

PHOTOGRAPH OF THIN LAYER CHROMATOGRAM (TLC)
(DETECTION UNDER UV-at 254 nm)

BHRINGRAJ (ECLIPTA ALBA)

PHOTOGRAPH OF THIN LAYER CHROMATOGRAM (TLC)
( DETECTION UNDER UV-at 254 nm)

BHRINGRAJ (ECLIPTA ALBA)

PHOTOGRAPH OF THIN LAYER CHROMATOGRAM (TLC)
( DETECTION UNDER UV-at 366 nm)

KALMEGH (ANDROGRAPHIS PANCICULATA)

PHOTOGRAPH OF THIN LAYER CHROMATOGRAM (TLC)
( DETECTION UNDER UV-at 254 nm)

KUTKI (PICRORRHIZA KURROA)

PHOTOGRAPH OF THIN LAYER CHROMATOGRAM (TLC)
( DETECTION UNDER UV-at 254 nm)

POLYHERBAL EXTRACTS SYRUP

PHOTOGRAPH OF THIN LAYER CHROMATOGRAM (TLC)
(DETECTION UNDER UV-at 254 nm)

POLYHERBAL EXTRACTS SYRUP

PHOTOGRAPH OF THIN LAYER CHROMATOGRAM (TLC)
(DETECTION UNDER UV-at 366 nm)

POLYHERBAL EXTRACTS SYRUP. EXTRACTS & MARKER COMPOUNDS

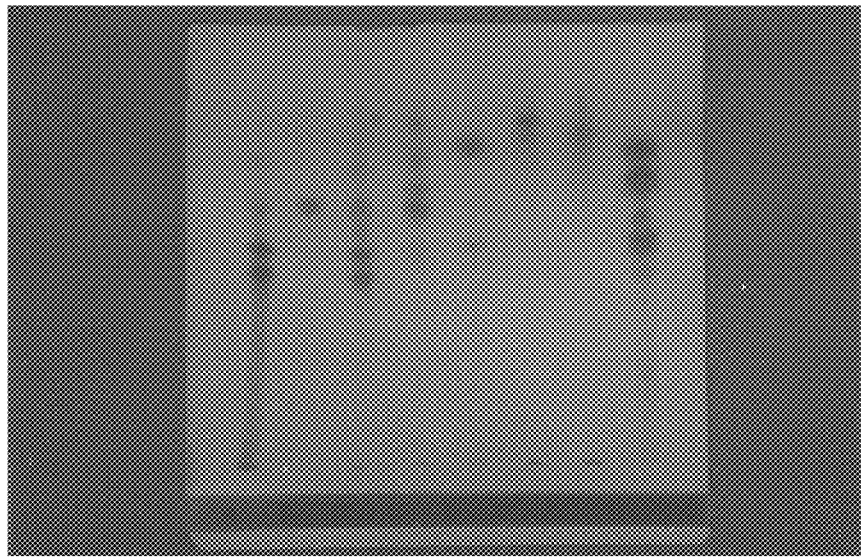

PHOTOGRAPH OF THIN LAYER CHROMATOGRAM (TLC)
( DETECTION UNDER UV-at 254 nm)

FIG.14

POLYHERBAL EXTRACTS SYROP. EXTRACTS & MARKER COMPOUNDS

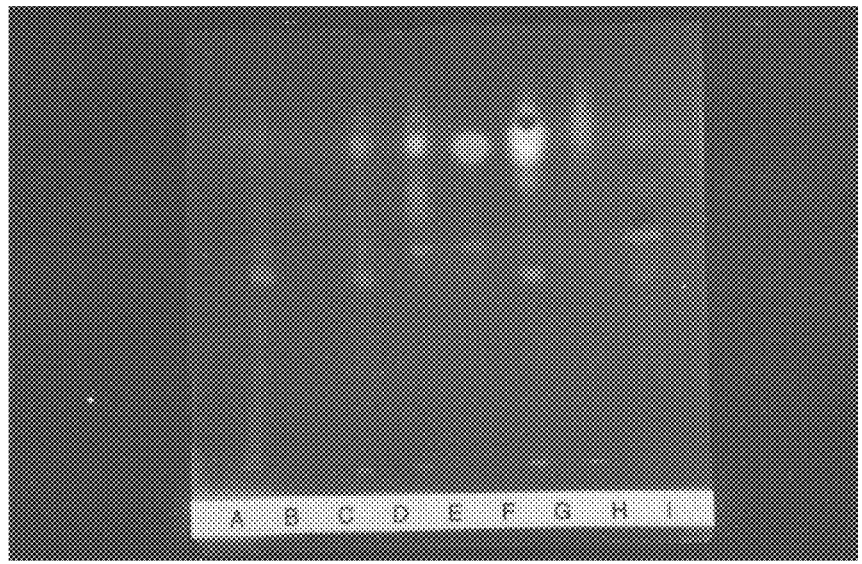

PHOTOGRAPH OF THIN LAYER CHROMATOGRAM (TLC)
( DETECTION UNDER UV-at 366 nm)

A=KUTKIN RS, B=ANDROGRAPHOLIDE RS, C=KUTKIN RM, D=ANDROGRAPHOLIDE RM, E=PHEUM EMODI RM, F=ECLIPTA ALBA RM, G=PHYLLANTHUS RM, H=POLYHERBAL EXTRACTS SYRUP, I=BLANK

FIG.15

HEPATOPROTECTIVE COMPOSITIONS AND COMPOSITION FOR TREATMENT OF CONDITIONS RELATED TO HEPATITIS B AND E INFECTION

FIELD OF THE INVENTION

The present invention relates to a novel polyherbal composition, a process for the preparation of the composition, a method of treating Acute hepatitis due to Hepatitis E virus (HEV), Healthy hepatitis B virus carrier with a super infection (Intercurrent) by hepatitis E virus resulting in acute hepatitis therapeutic effects on hepatitis B virus infection e.g. acute hepatitis associated with Hepatitis B virus, Hepatitis B virus healthy carrier state, Hepadna viridae e.g. Duck hepatitis B virus and its use as a hepatoprotective agent.

The present novel polyherbal hepatoprotective composition is derived essentially from four plants namely (1) *Phyllanthus amarus* Linn. (2) *Eclipta alba* Hassk (3) *Andrographis paniculate* Nees and (4) *Picrorhiza kurroa* Royle ex Benth.

In addition, the present invention provides a novel effective treatment of acute Hepatitis E virus infection, healthy Hepatitis B carrier developing an acute hepatitis E virus infection, acute Hepatitis B and chronic Hepatitis B carrier state, and also as a hepatoprotective agent as well as an agent for improving the cell line functions. This composition comprises essentially extracts from plants namely (1) *Rheum emodi* Wall, (2) *Phyllanthus amarus* Linn, (3) *Eclipta alba* Hassk (4) *Andrographis paniculate* Nees and (5) *Picrorhiza kurroa* Royle ex Benth. The plant *Phyllanthus amarus* Linn is also referred to as *Phyllanthus niruri* Linn.

BACKGROUND AND PRIOR ART RELATING TO THE INVENTION

The Ayurvedic system of Indian traditional medicine provides many formulations for treating many liver disorders/diseases in human beings and animals. Majority of these plants have already been investigated for their beneficial medicinal properties (Chopra, Nadkarni).

*Rheum emodi* Wall: *Rheum emodi* Wall is grown in sub Himalayan regions of India and its neighbouring countries. The traditional preparation consists of dried rhizome of the plant and roots which are cut into pieces and dried. Rhubarb root contains a large proportion of Chrysophanic acid, sometimes called Chrysophan. An allied substance Emodin, a glucose rhapantiein, a tannin named Rheo tannic acid, several resins, an albuminoid principle, mucilage. extractives, tannic and gallic acids, sugar, starch, pectin, lignan, calcium oxalate and various inorganic salts.

*Phyllanthus amarus* Linn (niruri): *Phyllanthus amarus* Linn (niruri) is a herbaceous plant which occurs as a winter weed throughout the hotter parts of India. The plant is bitter and astringent in taste, and the extract of the roots and the leaves are used as a remedy for jaundice and other related liver disorders. *Eclipta alba* Hassk: *Eclipta alba* Hassk is a herbaceous plant which grows in moist conditions throughout India. The extracts of *Eclipta alba* Hassk are largely used for the treatment of the liver, and the gall bladder diseases. The plant juice and extracts are also used in combination with other aromatics in the treatment of jaundice.

*Andrographis paniculate* Nees: *Andrographis paniculate* Nees is an annual herb which is grown as a hedge plant throughout the plains of India. The plant is reputed in the Ayurvedic system of medicine to be useful in the treatment of sluggish liver and jaundice.

*Picrorrhiza kurroa* Royle ex Benth: *Picrorrhiza kurroa* Royle ex Benth is a perennial herb found in the Alpine Himalayas from Kashmir to Sikkim. Its use in the Ayurvedic system of medicine is described in the disease states of jaundice, liver disorders and urinary disorders.

*Fumaria officinalis* Linn: *Fumaria officinalis* Linn is reputed to be useful in disorders of the liver, and is found throughout India, from the Indo-gangetic plain to the Nilgiri Hills.

*Tinospora cordifolia* Miers: *Tinospora cordifolia* Miers is a succulent climbing shrub and occurs in most pars of Southern India. The extracts of *T. cordifolia* Miers are effective in promoting the regeneration of liver tissue, and preventing fibrous changes occuling due to hepatotoxic injuly to Liver.

*Terminalis chebula* Retz: The fruits of this large deciduous tree are used for its purgative, tonic and carminative properties. In combination with *Embellica officinalis* and *Terminalia belerica*, under the Indian name TRIPHALA, these fruits are used as adjuncts to other medicines in the treatment of almost all disease states in the Ayurvedic system of medicine.

*Cichorium intybus* Linn: *Cichorium intybus* Linn is a rough and glandular perennial herb found throughout northwest India. The root of the plant is known to be useful in the disease states resulting in enlargement of liver and spleen.

*Tephrosia purpurea* Linn: The root of this branched herbaceous plant has been found to be useful in the treatment of sluggish liver by improving its function and also in enlarged spleen.

HEPATITIS VIRUSES

Acute hepatitis is usually viral in origin and is a diffuse necro-inflammatory disease of the liver as a result of infection by primary seven hepatotropic viruses namely hepatitis A (HAV), Hepatitis B (HBV) parenterally transmitted non-A non-B hepatitis (HEV), hepatitis F (HFV) and hepatitis G (HGV).

Present invention relates to Hepatitis E and Hepatitis B and relevant literature on these two agents is summarised below:

HEPATITIS E VIRUS (HEV)

The absence of serological markers for either Hepatitis A Virus (HAV) or Hepatitis B Virus (HBV) led to the recognition of a viral hepatitis agent(s) which were initially collectively grouped as non-A, non-B hepatitis (NANBH) virus(es). Two epidemiologically distinct forms of NANBH were identified which appeared to be transmitted by either (a) parenteral route or (b) faecal/oral route. The virus responsible for most cases of parenterally transmitted NANBH has been termed hepatitis C virus (HCV).

A second, epidemiologically distinct form of NANBH was referred to as enterically transmitted NANBH (ET-NANBH) (Mast & Krawczynki, 1996; Bradley, 1990; Balayan, 1990; Zukerman, 1990; Deinsteg, 1983 and Khuroo et al., 1983). Major outbreaks of ET-NANBH have occurred in Asia, the Soviet Union, North America and Africa. The etiological agent of ET-NANBH has been identified, cloned and termed the hepatitis E virus (HEV).

The first direct evidence for a new viral agent of ET-NANBH came in 1983 from human volunteers and Cynomolgus monkeys transmission studies. The feces inoculum was found by Immune Electron Microscopy (IEM) to contain 27–30 nm virus like particles which reacted to serum from the human and Cynomolgus monkeys during acute phase of the disease. Feces obtained during the course of the experimental infection were also found to contain 27–30 nm particles which reacted to acute phase sera from the monkeys, the human volunteer and the inoculum source individuals (Chauhan et al., 1993). The absence of a cell culture system lead to use of Cyno or human specimens for molecular cloning of the HEV agent.

The serological tests to diagnose acute HEV hepatitis as demonstrated by the presence of HEV-IgM/IgG have recently been commercially available. and been useful in identifying the aetiological agent in patients of acute hepatitis E virus infection (Favorov et al., 1996), healthy HBV carriers who develop a superadded (intercurrent) infection with HEV. The recent availability of the diagnostic tests for HEV infection (anti HEV IgM/IgG) will elucidate a clear epidemiological data, natural history of the disease and drugs/natural plant products which might be useful in therapeutic treatment for patients of acute HEV infection.

The first well characterized epidemic for HEV was in Delhi (Wing et al., 1980), India in 1955–56 in which 29300 individuals were involved. HEV has a worldwide distribution.

Large outbreaks of HEV infection generally occur in hopical climates and are usually associated with fecal contamination of drinking water caused by flooding during the mansoon or rainy seasons. The disease seems to have its highest attack in young adults (Tandon el al., 1982, 1985; Corwin et al., 1996).

More than 50 epidemics of Hepatitis E have been reported in 27 countries in Asian, African and North American continents over last 30 years. The source of HEV maintenance in an endemic area is not well understood.

Epidemics appear to be cyclical, occurring every few years in areas endemic for the virus probably due to short-lived immunity aquired after an exposure to HEV.

Sporadic HEV cases have been known to occur in the same geographical areas of epidemics (Mast & Krawczynki, 1996). Sporadic cases have also been reported among persons from Europe and the U.S. traveling to areas endemic for HEV. Sporadic HEV accounts upto 50% of clinical hepatitis in areas endemic for the HEV disease. If all of these cases are due to HEV then this viral agent is the most common cause of acute viral hepatitis occurring in the developing world.

The incubation period of HEV has a mean of about 6 weeks. The disease appears to be self limiting without the development of a chronicity or long tenn Liver sequelae. However, there is a much higher degree of morbidity and mortality associated with HEV than with HAV (Tandon et al., 1982; 1985). In epidemics it has been known to be as high as 1.2%.

The preicteric stage lasts for 1–10 days and this includes gastrointestinal symptoms such as pain, nausea, vomiting and loss of appetite. The icteric phase comprises of jaundice, dark urine and clay-coloured stools along with tender hepatomegaly. There is a gross alteration in liver function tests e.g. Serum Bilirubin, Serum Glutamic Pyruvic Transminase (SGPT), Serum Glutamic Oxaloacetic Transaminase (SGOT), and Alkaline Phosphatase along with the presence of anti HEV IgM which establishes aetiological diagnosis of the disease. This period usually lasts for about four weeks and complete recovery characterised by clinical improvement in signs and symptoms along with normalization of liver function tests occurs usually in approximately within three months after onset of symptoms.

There is a strong IgM response during the acute phase followed by a rise in IgG anti-HEV antibody, which begins to disappear after about 9 months post infection.

There is a high rate of fulminant hepatitis associated with HEV, particularly among pregnant woman in the third trimester with a fatality rate between 10–40% (Khuroo et al., 1983).

During last decade, rapid advances in development of serological tests for the laboratory diagnosis of different types of viral hepatitis has changed the aetiological understanding of acute liver failure. Hepatitis E virus is the commonest cause of acute liver failure in sporadic and endemic acute hepatitis occurring in India (Jaiswal, 1996). Other countries which are endemic for hepatitis E virus infection may also have a similar clinical situation.

Further, acute liver failure is more common in India than in any other country of the world (Tandon, 1996). Several contributing factors are thought to be responsible e.g. prevalence of a large pool of hepatotropic virus(es) undernutrition population, an unsatisfactory early diagnosis and availability of affordable treatment of acute hepatitis. These environmental settings may also be true for several other countries of the world with socio-economic conditions similar to India.

Histopathological examination of needle biopsy specimen obtained during the course of Hepatitis E have no features that distinguish this form from other forms of acute viral hepatitis (Gupta & Smetana, 1957).

HEV infection does not appear to lead to chronic liver disease but it can aggravate the course of chronic hepatitis B virus infection or produce a superinfection (intercurrent) in a healthy hepatitis B virus carrier state thereby resulting in increased morbidity and mortality.

The control measure for acute HEV hepatitis include provision of clean water supplies, safe disposal of human excreta and sound personal and food hygiene practices. Vaccines for hepatitis E are not available and prophylaxis with immune serum globin appears to have little or no protective effect.

The treatment for hepatitis E is supportive. No data is available to evaluate the efficacy of antiviral agents or any other specific therapies for treatment of hepatitis E.

After extensive research the applicants have invented for the first time that the present polyherbal pharmaceutical preparation derived essentially from five plants e.g. *Rheum emodi* Wall, *Phyllanthus amarus* Linn, *Eclipta alba* Hassk, *Andrographis paniculate* Nees and *Picrorhiza kurroa* Royle ex Benth, is useful in the treatment of Acute Hepatitis E virus infection in man, healthy carriers of Hepatitis B who develop superadded Hepatitis E virus infection. Further, the present composition is also effective in Hepatitis B virus infections.

In addition, the applicants notice that HEV is a cytotoxic and destroys the hepatocites (liver cells) i.e. necrosis of the liver cells. Further, the applicants observed that the polyherbal composition for the present invention is hepatoprotective in nature, they have devised for the first time a method to regenerate and protect the liver cells from necrosis by administering the present polyherbal composition to the patients.

HEPATITIS B VIRUS (HBV)

Hepatitis B virus is partially double stranded DNA virus that replicates in part through an RNA intermediate. The complete virus is known as Dane particle and measures 42 nm in diameter. This consists of a 27 nm core of an incomplete dsDNA surrounded by a coat of surface material.

Man is the natural source and reservoir of Hepatitis B virus infection. Hepatitis B virus is endemic in some population and hyperendemic in many parts of world. Chronic infection occurs in less than 2% of population in North America. Western Europe, Australia, whereas high prevalence rate is seen in Asia, the Pacific islands, parts of China and India. The source of infection is HBV infected blood or transmission by sexual route from infected mother to newborn (perinatal). All age groups and both sexes are susceptible. Endemicity exists and high risk groups include blood recipients, haemophilics, health care workers and children born to HBV infected mothers.

The incubation period of acute HBV hepatitis is 4–18 weeks. The first marker appearing in blood is HBsAg followed by a high rise in transaminase levels. HBV infection may also lead to both asymptomatic and severe form of liver diseases. Around 5–10% of acute HBV infected population become chronic carriers. HBV carrier stage is common if the exposure occurs in early childhood. Most of the infections are acquired in early childhood, usually as mother to child transmission, and results in a persistent HBV carrier stage.

There are more than 200 million Hepatitis B virus carriers in world, who besides developing a chronic liver disease (chronic hepatitis, cirrhosis, hepatocellular carcinoma) as a result of persistent HBV infection are also at a constant risk of acquiring a super infection with other hepatotropic viruses which might worsen their clinical condition. Infection with Hepatitis Delta Virus, hepatitis non-A, non-B [both Hepatitis C virus (HCV), Hepatitis E virus (HEV) and hepatitis A virus (HAV)] are hazardous to healthy the carriers of hepatitis B virus. In developed countries e.g. Italy, France, England and United States, Hepatitis Delta or Hepatitis C virus have been found to be major aetiological factors which usually lead to super infection in HBV carriers.

In contrast, the high prevalence of HEV in the Indian continent and developing world and being the major aetiological agent responsible for acute viral hepatitis, it has been postulated to present a big risk of intercurrent or superadded infection in a HBV carrier which might lead to severe liver injury (Tandon et al., 1984). At present, no effective therapy is available for such a group of healthy hepatitis B virus carriers who are super infected with Hepatitis E virus and develop acute hepatitis.

The only way of gradually eradicating the infection is by (1) active universal immunisation in childhood and/or (2) development of treatment modalities for persistently infected persons. Therapeutic studies conducted over the past 15–20 years had only marginal success once the infection is establishede (Hoofnagle, 1991). Several compounds, such as interferon, adenine arabinoside, acyclovir, ganciclovir, zidovudine and immunomodulatory regime administered alone or in combination have been evaluated. Most of these agents have transient effects on viremia, with rebound occurrence on withdrawal of drug. Signifcent toxicity have also been observed with long term therapy.

Hepatitis B Virus Infection and Natural Plant Products

Many plant products have been in use in the treatment of liver diseases since time immemorial. In Indian systems of medicine, natural plant products have been used in the treatment of jaundice and liver disorders. The use of various plants have been described in ancient Indian Ayurvedic literature.

In South India, the plants of genus Phylianthus and *Eclipta alba* Hassk are commonly used as a traditional treatment for clinical jaundice including that of viral hepatitis and are commercially available (Thyagarajan, 1986; Thyagarajan & Jayaram, 1992). Phyllanthus species are also used in China, the Philippines, Cuba, Nigeria, Guam, East and West Africa, the Carribean, Central America and South America. The above two plants have been recently evaluated for their action on Hepatitis B virus. The first screening strategy used was to test the ability of plant extract to coat viral HBsAg, and thereby inhibit the reaction with antibody to HBsAg (anti HBs like activity) (Unander and Blumberg, 1991; Blumberg et al., 1990). The rationale was that such an inhibition might have effect on pathogenesis of Hepatitis B virus in vivo in man (Mehrotra et al., 1990, 1991). This observation was also supplemented by the ability of plant extract to inhibit DNA polymerase (DNAp) of Hepatitis B virus in vitro.

The crude extracts of *Eclipta laba* Hassk when mixed with HBsAg brings about its interaction, thereby suggesting the presence of anti HBs like activity (Thyagarajan el al., 1982).

The extracts of *Phyllanthus niruri* Linn now known as *Phyllanthus amarus* Linn inhibit human HBV-DNAp as well as HBsAg and anti HBs interaction. Also, the closely related animal hepadna viruses, e.g. Woodchuck hepatitis virus, and duck hepatitis B virus are also affected by *P. amarus* Linn (Blumberg et al., 1990). In a series of studies on long term carriers of woodchucks infected with woodchuck hepatitis B virus it was observed that the *P. amarus* Linn extract generally eliminates or decreases the level of virus (Venkateshwaran et al., 1987; Venkateswaran and Blumberg—U.S. Pat. No. 4673575, 1987). However, subsequent studies using another animal model of Human Hepatitis B virus, Duck hepatitis B virus failed to confirm the findings reported earlier [Nitu et al., 1990; Munshi et al., 1993(a),(b)].

Clinical studies in humans using *P. amarus* Linn, on Hepatitis B virus has also been carried out. In 1988, it was reported from Madras, India that dried milled *P. amarus* Linn was successful in clearing Hepatitis B surface antigen from 59% carriers of Hepatitis B virus (Thyagarajan el al., 1990). However, this observation was followed by another report wherein the success rate of treatment with *P. amarus* Linn was reduced to 20% (Thyagarajan et al., 1990). In subsequent clinical studies on Hepatitis B virus carriers with *P. amarus* Linn, results were not reproducible by other workers in different other countries (Brook, 1988; LeeLarasamee et al., 1990; Mei-Xia et al., 1991; Milne et al., 1993).

Traditional plant medicines have also been tested for suppression of viral antigen secretion by Alexander Cell line obtained from human hepatocellular carcinoma (PLC/PRF/5), which contain several integrated copies of HBV genome and produces small amount of HBsAg apparently in the form of 22 nm particles. Goto et al. (1996) using the above cell line as a model tested forty three (43) extracts of different herbal medicines for suppression of secretion of HBsAg in vitro. Of the various extracts, *Rheum palmatum* L also suppressed the secretion of HBsAg. However, the above observation is never substantiated/established in any in-vivo animal model of Hepatitis B virus infection and also in human studies.

Animal Models of Hepatitis B Virus Infection

Though HBV was discovered to be the causative agent of Hepatitis B almost 30 years ago, however, a detail understanding of the biology of this clinically important virus has only developed in the last ten years. Among the problems faced by the early researchers were limited host range, and lack of tissue culture system in which to propagate the virus.

The advent of molecular cloning techniques and the discovery of HBV like viruses in certain animals lead to rapid advances in late 1970s. Soon after the structure and sequence of HBV-DNA was determined. HBV like viruses in animals other than man were discovered. HBV and similar DNA viruses which differ from known class of animal DNA viruses were collectively grouped under *Hepadna viridae* (Gust et al., 1986). Among the features which define the family are unique viron ultrastructure, polypeptide and antigenic composition, common genome size, similar structure and replicating mechanism in hepatocyte and extrahepatic tissue. The first animal hepadna virus was isolated from Woodchuck by Summers and coworkers in 1978. This followed an earlier observation by Robert Snyder that a high proportion of Woodchucks which died at Philadelphia zoo had liver tumours. Viral particles isolated from woodchuck sera exhibited a similar size and morphology to those described for HBV. The woodchuck virus particles were shown to be serologically related to HBV, and also contain an endogenous polymerase activity and a genome of similar size and structure to HBV.

A similar high incidence of liver tumour in domestic ducks in China lead to identify a second animal Hepadna virus—Duck Hepatitis B virus. Attempts to transmit the duck hepatitis B virus (DHBV) revealed unexpected results that approximately 10% of domestic ducks in the United States were congenitally infected with virus (Summers, 1987).

At about the same time, a third hepadna virus was identified in beechy ground squirrel (GSHV) in California (Morion et al., 1980). Hepadna virus have also been reported in tree squirrels (Mehrotra et al., 1990; Feitelson et al., 1980).

Duck hepatitis B virus (DHBV) infection is accompanied by the presence of large number of viral specific particles in the blood. The basic structure of DNA genome of *Hepadna viridae* is conserved in DHBV (Mason et al., 1980). The average transmission occurs through egg from a carrier mother. In avians the host immune system develops 3 to 5 days post hatch and therefore 24 hours old ducklings are ideal candidates for transmission studies. If the DHBV infection occurs just after egg hatching the animal become persistently viremic. It is therefore, possible using this experimental model of HBV to evaluate any compound/preparation for its effects on carrier state.

DHBV has been used as a model for the evaluation of antiviral chemotherapies against human hepatitis B virus infection (Zuckerman, 1987) and also the natural plant products (Munshi et al., 1993, 1994). Several antiviral agents have been evaluated in chronically infected ducks (Hirota et al., 1987). DHBV infection has been associated with a broad spectrum of liver pathology e.g. chronic hepatitis, cirrhosis and hepatocellular carcinoma (Mehrotra et al., 1987; Duflot et al., 1995).

The ultimate aim of therapy with HBV infection is to render patients less infectious which helps in recovery, thereby the development of chronic sequelae (Cirrhosis, hepatocellular carcinoma) can also be prevented.

A positive therapy should aim towards reduction in HBV replication. This activity can be assessed by demonstrating a decrease in serum HBV-DNA, clearance of HBeAg and HBsAg. So far, there is no effective and economical treatment for Hepatitis B virus infection, its carrier state, and superadded infection by other Hepatitis viruses e.g. HEV.

Due to the graveness of the above problem, the applicants started investigating the native Indian plants since 1970 and formulated a useful herbal composition comprising nine Indian plants, each of which comprising 10 to 20 mg per dosage, in the composition. Unfortunately, this formulation did not produce the desired results and hence, a need was felt to do further research in order to produce a new composition targeted against Hepatitis and viral hepatitis.

OBJECTS OF THE INVENTION

The objects of this invention relates to a polyherbal pharmaceutical composition comprising essentially plants namely *Rheum emodi* Wall, *Phyllanthus amarus* Linn, *Eclipta alba* Hassk, *Andrographis panciulate* Nees, and *Picrorhiza kurroa* Royle ex Benth in treatment of acute hepatitis caused by Hepatitis E virus, a super infection due to Hepatitis E virus in healthy Hepatitis B carrier state in man.

Another object of the invention relates to a method of regenerating and protecting the liver cells from necrosis by using polyherbal composition of the present invention.

Still, another object of the invention is for providing a pharmaceutical composition comprising extracts of *Rheum emodi* Wall for the treatment of acute and chronic and persistent hepatitis B viral infection in human being or animal hepadna virus e.g. Duck hepatitis B virus.

Yet, another object of the invention relates to a pharmaceutical composition useful for the treatment of hepatitis B virus infection, which comprises of fraction of *Rheum emodi* Wall, said fraction having anti HBsAg, anti HBeAg like activity and also produces an effect on HBV-DNA.

Further object of the invention relates to a pharmaceutical composition for treatment of hepatitis B virus infection which comprises of aqueous extract of *Rheum emodi*, said fraction having effect on clearance/intermittent effects on viremia of HBV in human beings and animal hepadna model such as Duck hepatitis B virus.

One more object of the invention is to provide a process for preparing a polyherbal pharmaceutical composition comprising essentially plants namely *Rheum emodi* Wall, *Phyllanthus amarus* Linn, *Eclipta alba* Hassk, *Andrographis panciulate* Nees, and *Picrorhiza kurroa* Royle ex Benth in treatment of acute hepatitis caused by Hepatitis E virus, a super infection due to Hepatitis E virus in healthy Hepatitis B carrier state in man and in treatment of acute and chronic and persistent hepatitis B viral infection in human being or animal hepadna virus.

Another object of the invention relates to a method of treating acute Hepatitis E virus infection,healthy hepatitis B carriers with superadded Hepatitis E virus and carriers of Hepatitis B virus.

Additional object of the invention provides a method of treating acute and chronic viral Hepatitis and theraptic effects of hepatitis B virus infection.

One more object of the invention relates to a method treating acute liver failure cause due to hepatitis E virus infection and a method of protecting liver cells against known chemicals/durgs which cause liver injury.

The polyherbal pharmaceutical composition of the present invention is safe without any toxic effects, also provides hepatoprotection in acute hepatotoxicity produced by known hepatotoxins in animals including human beings.

SUMMARY OF THE INVENTION

To meet the above objects, the present invention provides a novel polyherbal composition comprising essentially of extracts derived from plants namely *Rheum emodi* Wall, *Phyllanthus amarus* Linn, *Eclipta alba* Hassk, *Andrographis paniculate* Nees and *Picrorhiza kurroa* Royle ex Benth; a process for preparing such novel polyherbal composition, and a method of treatment of acute hepatitis E virus, chronic healthy carrier of Hepatitis B virus developing a superadded acute Hepatitis E virus infection, acute hepatitis B virus infection, Hepatitis B carrier state and hepatoprotection employing said polyherbal composition.

DETAILED DESCRIPTION OF THE INVENTION

Figure 1:
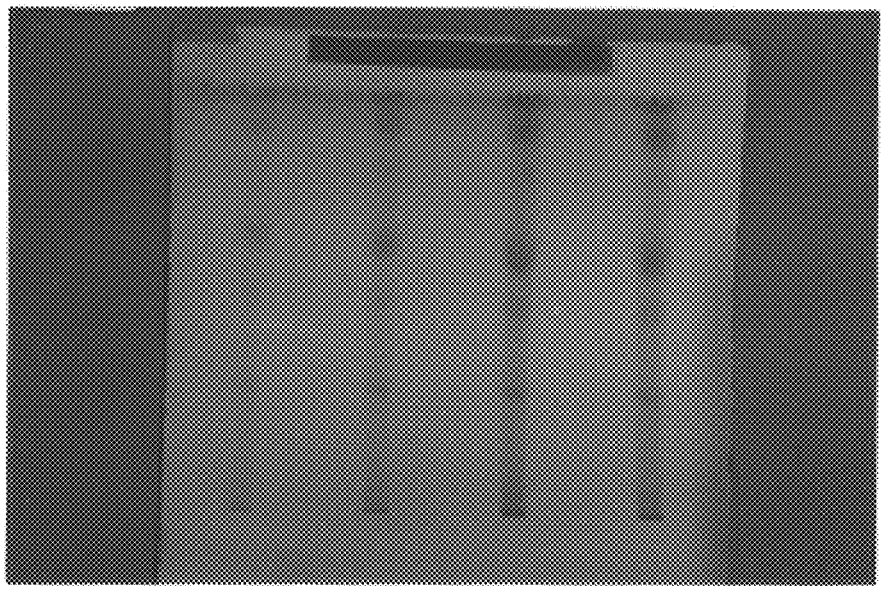

The invention provides a novel hepatoprotective composition comprising essentially extracts of *Rheum emodi* Wall, *Phyllanthus amarus* Linn, *Eclipta alba* Hassk, *Andrographis paniculate* Nees and *Picrorhiza kurroa* Royle ex Benth and optionally includes one or more extracts of plants selected from *Fumaria officinalis* Linn, *Tinospora cordifolia* Miers, *Terminalia chebula* Retz, *Cichorium intybus* Linn, *Tephrosea purpurea* Linn and *Boerhaavia diffusa* Linn. This composition is useful for the treatment of acute Hepatitis E virus infection, super infection of Hepatitis E virus in hepatitis B healthy carrier state or persistent Hepatitis B virus infection.

The invention also provides a novel hepatoprotective and anti viral composition essentially comprising extracts of *Rheum emodi* Wall, *Phyllantus* Linn, *Eclipta alba* Hassk, *Andrographis paniculate* Nees, and *Picrorhiza kurroa* Royle ex Benth.

The invention also relates to a method of treating patients suffering from acute hepatitis E virus, B virus infection, hepatitis B virus healthy carriers who develop hepatitis E virus super infection and the treatment consists of administering to the patients the present novel polyherbal pharmaceutical composition.

Further, the invention relates to the preparation of polyherbal phannaceutical composition which produces effects on humans or animal model of Hepatitis B (*Hepadna viridae*) virus persistent carrier state such as Duck Hepatitis B virus. It does not produce any toxicity to systemic parenchymatous organs of the body e.g. Heart, Kidney, Lung, Pancreas and Gastrointestinal tract.

In addition, the invention relates a polyherbal pharmaceutical composition which provides protection from the acute hepatotoxic effects of hepatotoxins such as Galactosamine, paracetamol, Thioacetamide, Rifampicin and Isoniazid, Aflatoxin B1, to the liver.

Moreover, the invention also relates to a process for the preparation of a novel polyherbal composition by mixing in any known manner the extracts of *Rheum emodi* Wall, *Phyllanthus amarus* Linn, *Eclipta alba* Hassk, *Andrographis paniculate* Nees, and *Picrorhiza kurroa* Royle ex Benth. In addition, the process includes adding optional ingredients such as extracts of plants namely *Fumaria officinalis* Linn, *Tinospora cordifolia* Miers, *Terminalia chebula* Retz, *Cichorium intyhus* Linn, *Tephrosea purpurea* Linn and *Boerhaavia diffusa* Linn. The solvents used in the extracion of the above plants may be ethanol, methanol, chloroform, ethylacetate, water or mixture thereof.

The applicants notice that the pharmaceutical composition of the present invention is useful in treating of hepatitis B virus infection and such composition includes fraction of *Rheum emodi*. The fraction of *Rheum emodi* contains extractable components of this plant which also possesses Hbs, anti Hbe like activity and apart an effect on HBV-DNA.

The invention provides a method of treating acute liver failure caused due to Hepatitis E virus infection by administering orally the polyherbal composition. In addition, the present composition provides hepato protection against known chemicals/drugs which are normally causes liver injury.

The present invention is illustrated with reference to the following examples and these examples should never be construed to limit the scope of the present invention. In other words, the following examples are merely to illustrate the present invention and such examples do not in any manner restrict the scope of the invention.

EXAMPLE 1

Describes the Composition and Preparation of Polyherbal Pharmaceutical Plant Extracts:

Pharmaceutical Composition and Preparation of Plant Extracts

The plant extracts which are mixed together to obtain the present novel composition can be obtained by any known manner. All batches of plants used in the preparation of the present novel composition were botanically authenticated. The solvent used in the extraction of the plants may be any suitable solvent such as ethanol, methanol, chloroform, water or mixtures thereof.

The plants extract can be obtained by any known manner. Preferably, the whole plants and parts thereof were powdered and extracted with water. The extract was evaporated under reduced pressure below 50° C. leaving a residue. For human administration, the residue is mixed with pharmaceutically acceptable neutral excepients and converted into suitable oral dosage form. As regards the animal studies, the residue was mixed with water, kept overnight at 37° C. with stirring and extract was centrifuged at 10,000 rpm. The solution thus obtained was vacuum dried and dry weight of extract of each plant was determined. This dry extract was dissolved in a fixed volume of normal saline to make a stock solution and stored at 4° C. The stock solution of each plant extract was used to prepare the present novel composition.

Alternatively, the method of preparing the novel compositions comprising blending and extracting in any known manner all the plants or plant matrials obtained from all plants thereof.

The hepatoprotective herbs used for the formulation of the present composition contains the extracts, preferably aqueous extracts, of the following:

| Common Name | Botanical Name | Range of extract in mg per dose |
|---|---|---|
| Bhumyamalaki | *Phyllanthus amarus* Linn. | 25–250 |
| Bhringraj | *Eclipta alba* Hassk | 25–250 |
| Kalmegh | *Andrographis paniculate* Nees | 25–250 |
| Kutki | *Picrorhiza kurroa* Royle ex Benth | 25–250 |

What is unexpected in the present invention is that earlier, the above four plant extracts were combined in the range of 10 to 20 mg individually, the hepatoprotective property of this combination is identified only when the amounts of these ingredients are enhanced to the range of 25 to 250 mg per dose. In other words, the applicants for the first time noticed the hitherto unknown hepatoprotective property of the composition comprising extracts of plants namely *Phyllanthus amarus* Linn, *Eclipta alba* Hassk, *Andrographis paniculate* Nees and *Picrorhiza kurroa* Royle ex Benth when the amounts of these plant extracts are enhanced to the rage of 25 to 250 mg per dose.

The present invention also provides a hepatoprotective and anti hepatitis B virus composition comprising the following plant extracts.

| Common Name | Botanical Name | Range of extract in mg per dose |
|---|---|---|
| Revand chini | *Rheum emodi* Wall | 25–250 |
| Bhumyamalaki | *Phyllanthus amarus* Linn | 25–250 |
| Bhringraj | *Eclipta alba* Hassk | 25–250 |
| Kalmegh | *Andrographis paniculate* Nees | 25–250 |
| Kutki | *Picrorhiza kurroa* Royle ex Benth | 25–250 |

The above novel compositions also comprising optional ingredients such as extracts, preferably aqueous extracts of the following plants:

| Common Name | Botanical Name | Range of extract in mg per dose |
|---|---|---|
| Pitpapra | *Fumaria officinalis* Linn | 5–50 |
| Gilo | *Tinospora cordifolia* Miers | 5–50 |
| Haritaki | *Terminalia chebula* Retz. | 5–50 |
| Kasni | *Cichorium intybus* Linn | 10–50 |
| Sarpaunkha | *Tephrosea purpurea* Linn | 10–50 |
| Punarnava | *Boerhaavia diffusa* | 10–50 |

The most preferred method of preparing the polyherbal composition in tablet form is given below:

COMPOSITION

| Ingredients | Qty. of crude Herb/Tablet | Qty of crude Herbs for 2 million tablets |
|---|---|---|
| Revand chini (*Rheum emodi* Wall) | 170 mg | 34 kg |
| Bhringraj (*Eclipta alba* Hassk) | 300 mg | 60 kg |
| Bhumyamalaki (*Phyllanthus amarus* Linn) | 300 mg | 60 kg |
| Sarpaunkha (*Tephrosea purpurea* Linn.) | 180 mg | 36 kg |
| Kasni (*Cichorium intybus* Linn.) | 180 mg | 36 kg |
| Punarnava (*Boerhaavia diffusa* Linn.) | 100 mg | 20 kg |
| Gilo (*Tinospora cordifolia* Miers) | 72 mg | 14.4 kg |
| Haritaki (*Terminalia chebula* Retz.) | 72 mg | 14.4 kg |
| Kalmegh (*Andrographis peniculate* Nees.) | 60 mg | 12 kg |
| Kutki (*Picrorrhiza kurroa* Royle ex Benth.) | 60 mg | 12 kg |
| Pitpapra (*Fumaria officinalis* Linn.) | 30 mg | 6 kg |
| Total | | 304.8 kg |

1. EXTRACTION

The above mentioned herbs were weighed accurately and reduced to moderately coarse powder. The herbs (304.8 kg) were extracted in a steam jacketed boiling pan using 8–9 times purified water for 3.0 hours and filtered. The marc was again subjected to extraction as earlier using 6–7 times purified water for three more hours and filtered and both the filtrates were combined together.

2. CONCENTRATION, DRYING AND PULVERISATION OF HERBAL EXTRACT

The combined filtrate was concentrated and dried by spray drying method where no excipient is used. Sometimes, it is dried by tray drying method also where the combined filtrate is concentrated to a semisolid consistency and was poured on to a thin bed of Starch-Microcrystalline cellulose powder (each 10% of herbal extract) over trays of electric tray drier and dried at 70–80° C. The dried extract was pulverised through micro-pulveriser and sieved through No. 40 sieve.

3. GRANULATION

Powdered herbal extract was mixed with inert diluents like Microcrystalline cellulose, Calcium carbonate and granulated using starch-gelatin paste.

4. DRYING AND SIZING OF GRANULES

The granules were dried in electric tray drier at 60° C. and the entire quantity of granules were passed through No. 16 sieve.

5. COMPRESSION

The granules were mixed with lubricants like Starch, Talc and Magnesium stearate and compressed on Rotary Tablet Compression Machine using circular deep concave punches.

The most preferred method of preparing the present polyherbal composition in the form of a syrup is given below:

COMPOSITION

| Ingredients | Qty. of crude Herb/Tablet | Qty of crude Herbs for 400 Liter Syrup |
|---|---|---|
| Revand chini (*Rheum emodi* Wall) | 170 mg | 13.6 kg |
| Bhringraj (*Eclipta alba* Hassk) | 300 mg | 24 kg |
| Bhumyamalaki (*Phyllanthus amarus* Linn) | 300 mg | 24 kg |
| Sarpaunkha (*Tephrosea purpurea* Linn.) | 180 mg | 14.4 kg |
| Kasni (*Cichorium intybus* Linn.) | 180 mg | 14.4 kg |
| Punarnava (*Boerhaavia diffusa* Linn.) | 100 mg | 8.0 kg |
| Gilo (*Tinospora cordifolia* Miers) | 72 mg | 5.76 kg |
| Haritaki (*Terminalia chebula* Retz.) | 72 mg | 5.76 kg |
| Kalmegh (*Andrographis peniculate* Nees.) | 60 mg | 4.8 kg |
| Kutki (*Picrorrhiza kurroa* Royle ex Benth.) | 60 mg | 4.8 kg |
| Pitpapra (*Fumaria officinalis* Linn.) | 30 mg | 2.4 kg |
| Total | | 121.92 kg |

1. EXTRACT

The above mentioned herbs were weighed accurately and reduced to moderately coarse powder. The herbs (121.92 kg) were extracted in a steam jacketed boiling pan using 8–9 times purified water for 3.0 hours and filtered. The marc was again subjected to extraction as earlier using 6–7 times purified water for three more hours and filtered and both the filtrates were combined together.

2. CONCENTRATION AND SEDIMENTATION OF HERBAL EXTRACT

The combined filtrate was concentrated to about 50 litres and cooled to room temperature. Pectic enzyme (0.5% v/v) was added to said herbal extract, mixed well and set aside for sedimentation undisturbed for 72 hours. After 72 hours the supernatant was decanted.

3. PREPARATION OF SYRUP

A syrup base consisting of 60% w/v Sugar was prepared and cooled to about 50–55° C. and the said herbal extract was added and mixed well. It was then filtered through sparkler filter press using Celite and Dicelite over filter cloth. The final volume of the syrup was made up with purified water and mixed well.

The polyherbal composition of the present invention is administered orally in any suitable forms such as extracts, syrups, capsules, tablets and powders. The dosage of polyherbal composition may vary between 250–1000 mg per day which may be administered in 2 or more equitable dosages. The composition of the invention is as such a synergistic one and it can be mixed with any conventional additives such as flavouring agent, base or colouring agent. The composition of the present invention is also used as a hepatoprotective agent against known chemicals/drugs such as antituberculosis or oral contraceptives.

BRIEF DESCRIPTION OF THE ACCOMPANYING DRAWINGS AND IN THESE DRAWINGS:

The file of this patent contains at least one drawing executed in color. Copies of this patent with color drawing (s) will be provided by the Patent and Trademark Office upon request and payment of necessary fee.

Figure 2:
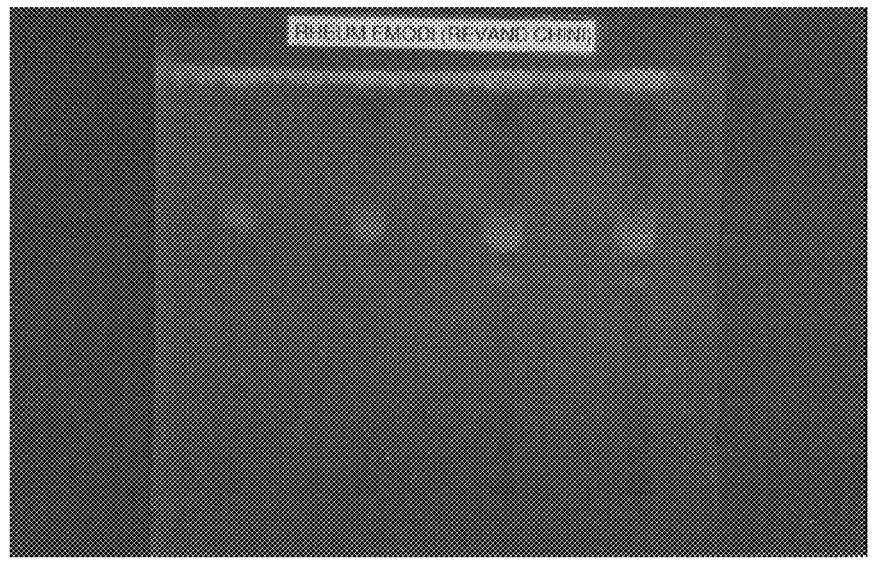
Figure 3:
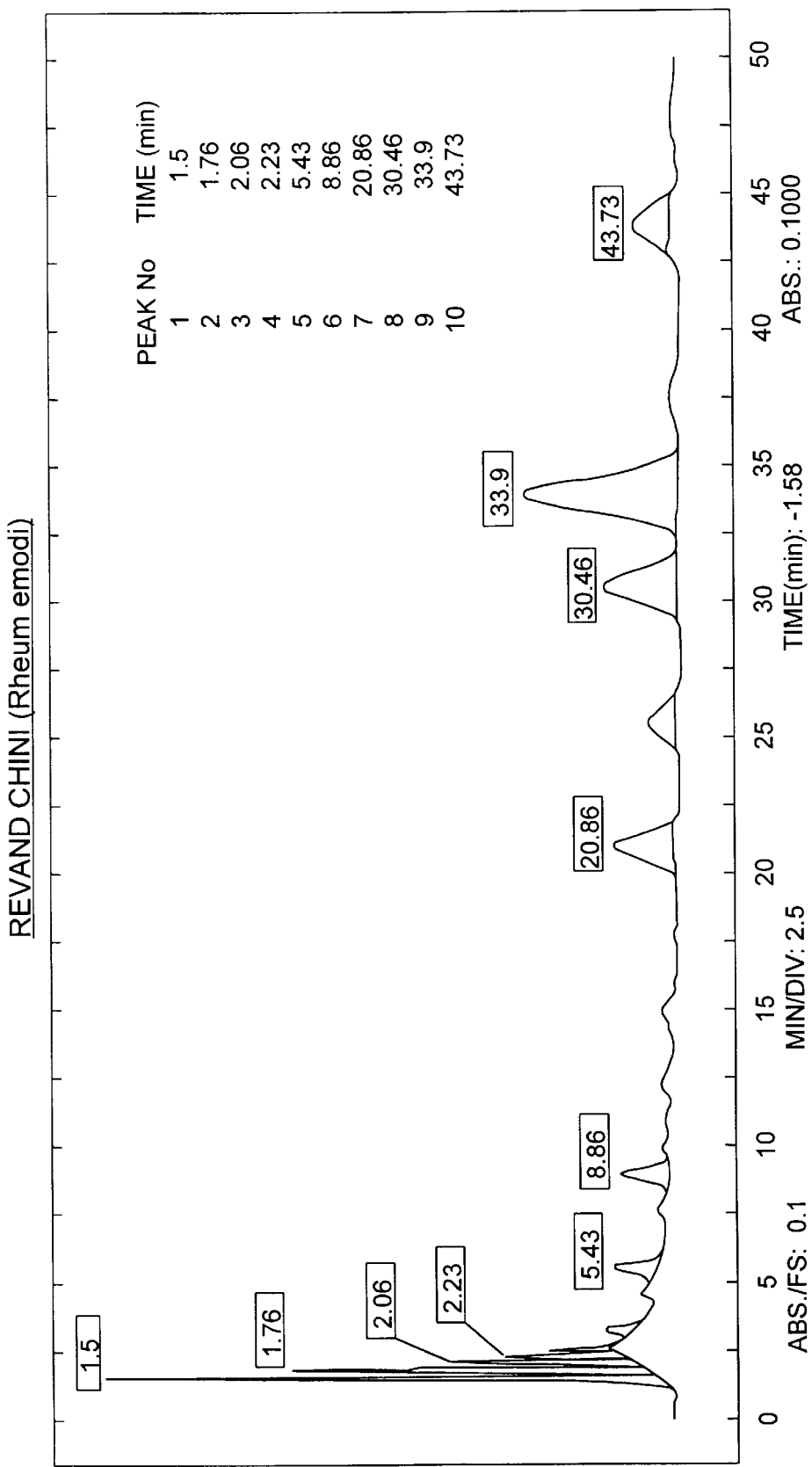
Figure 4:
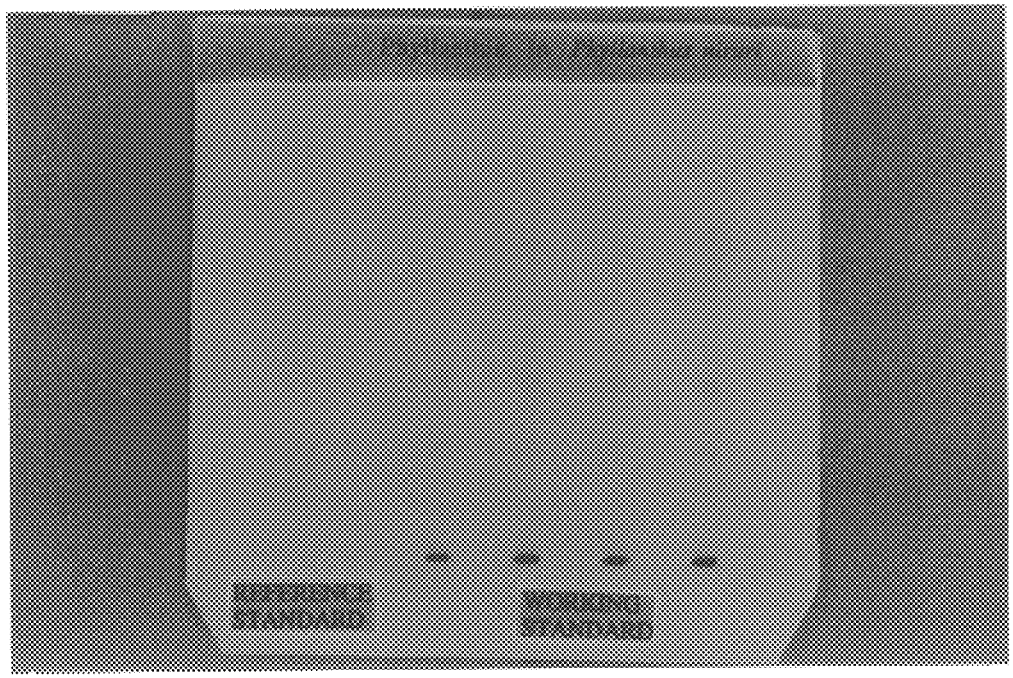
Figure 5:
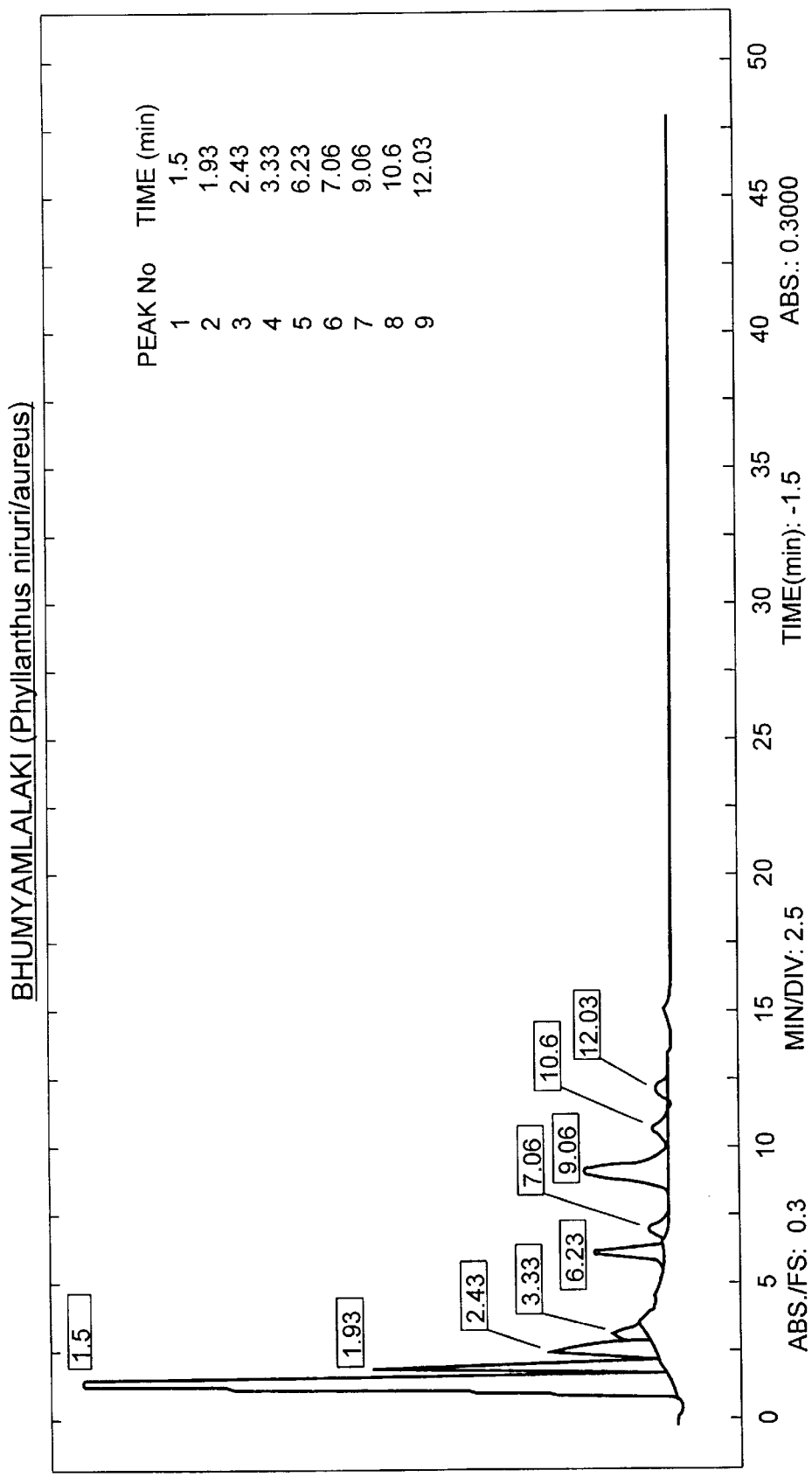
Figure 6:
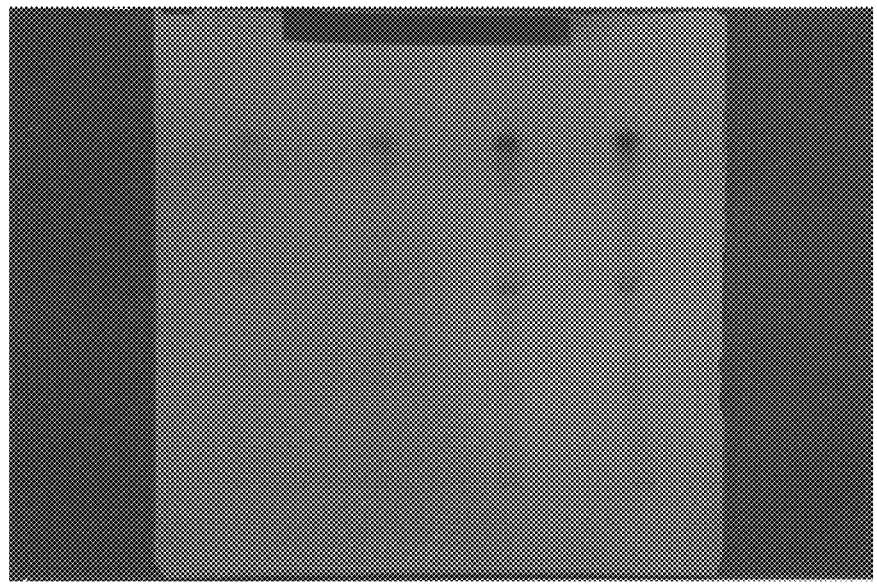
Figure 7:
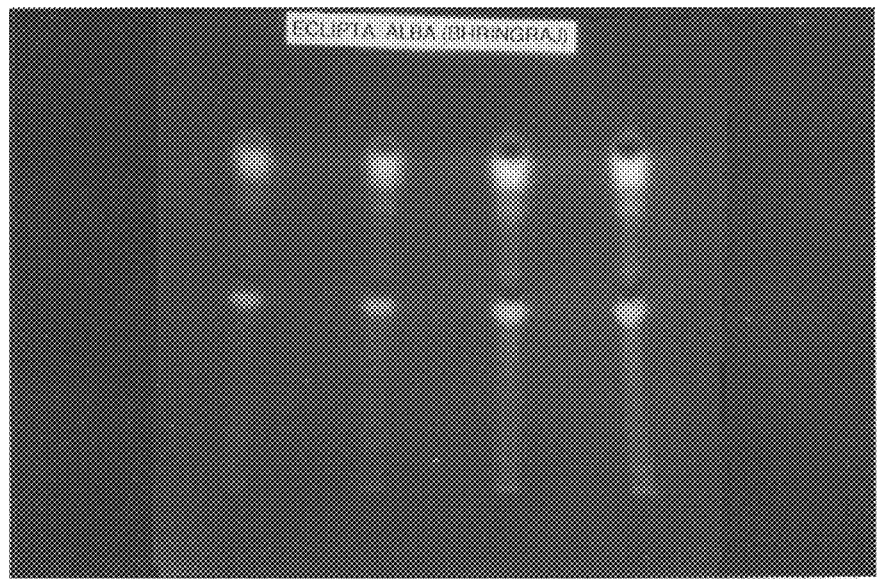
Figure 8:
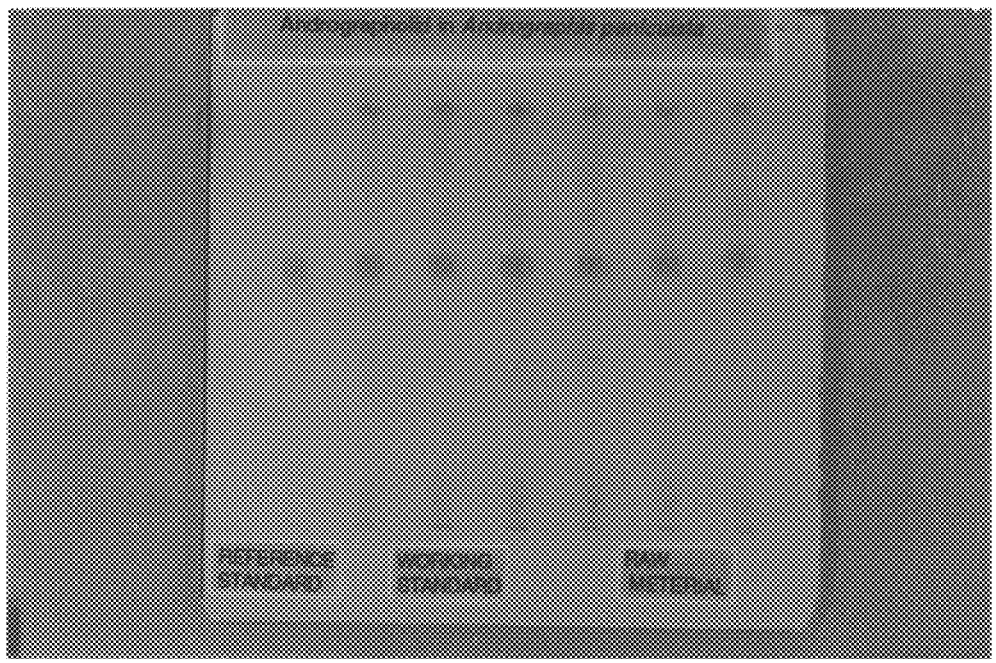
Figure 9:
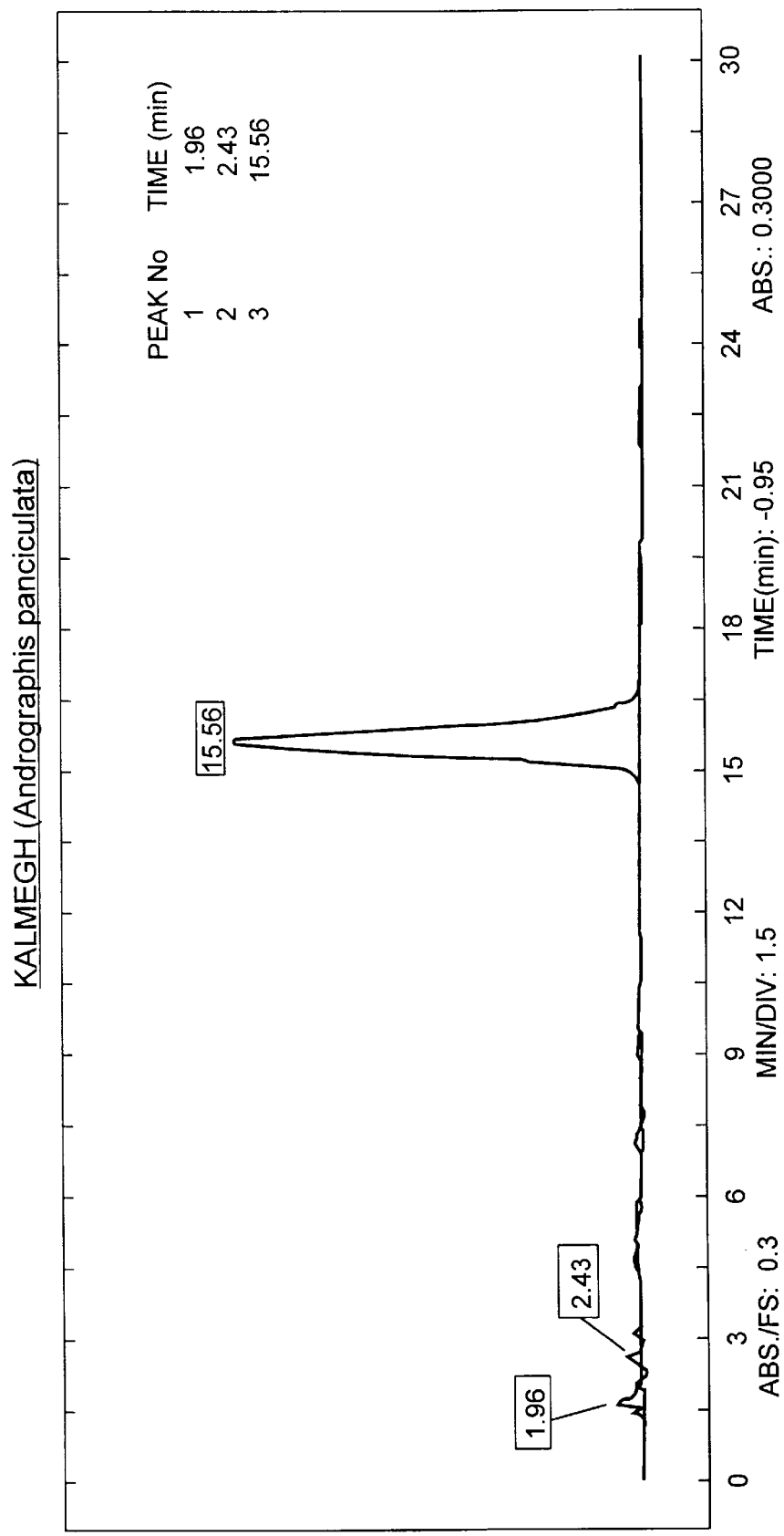
Figure 10:
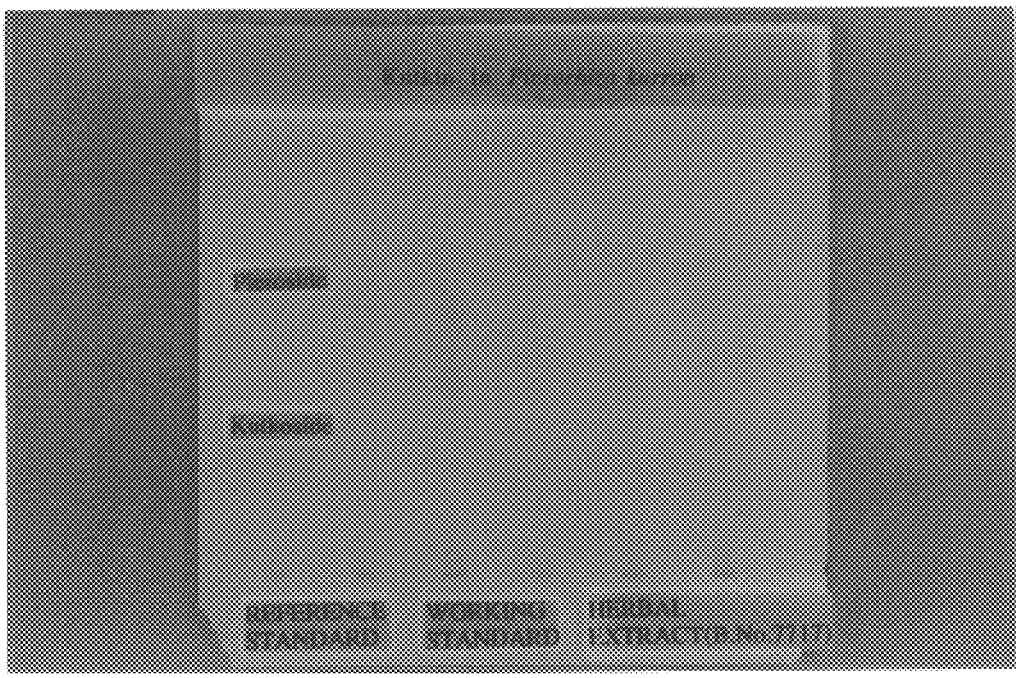
Figure 11:
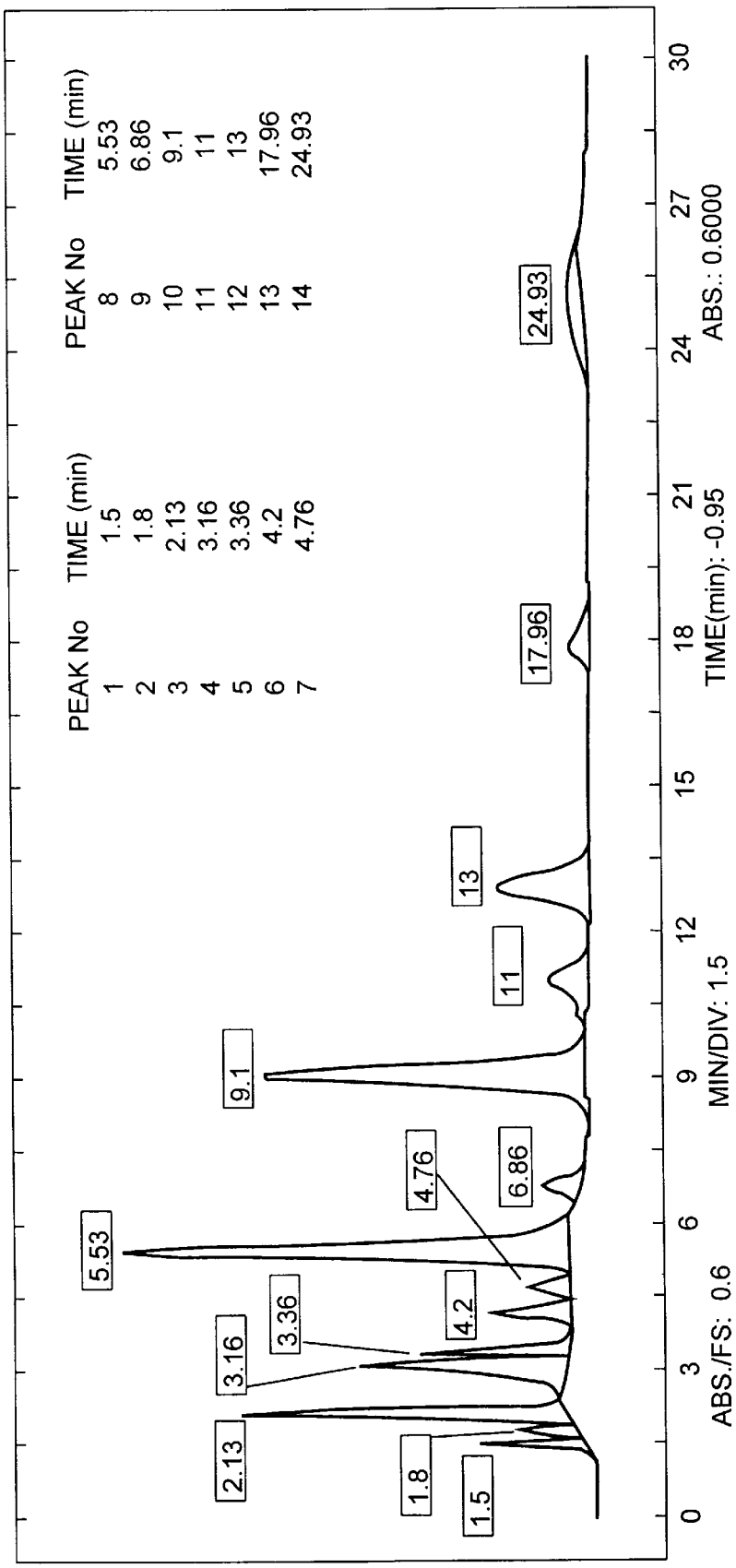
Figure 12:
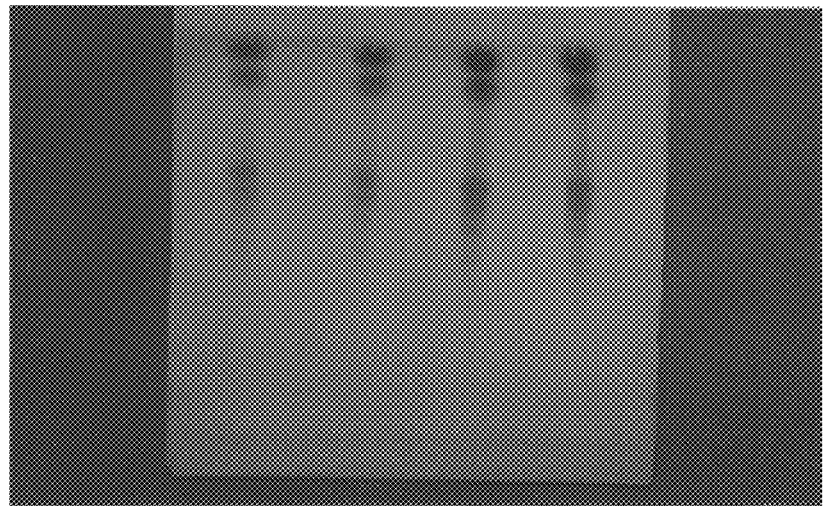
Figure 13:
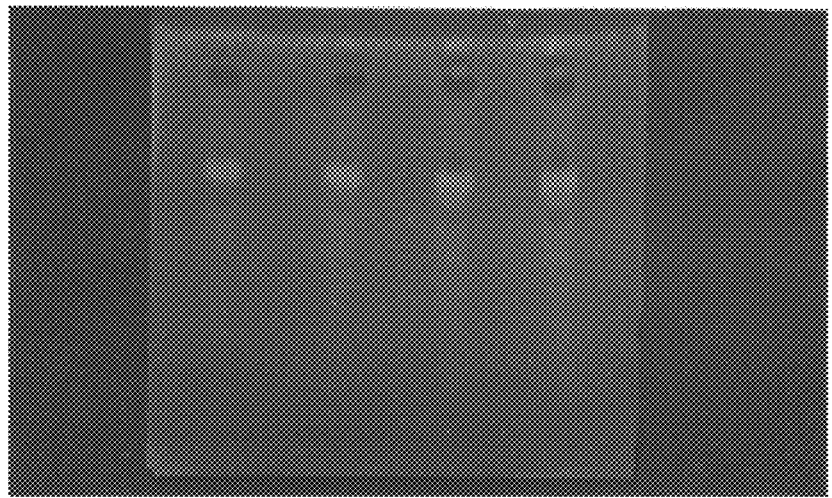
Figure 16:
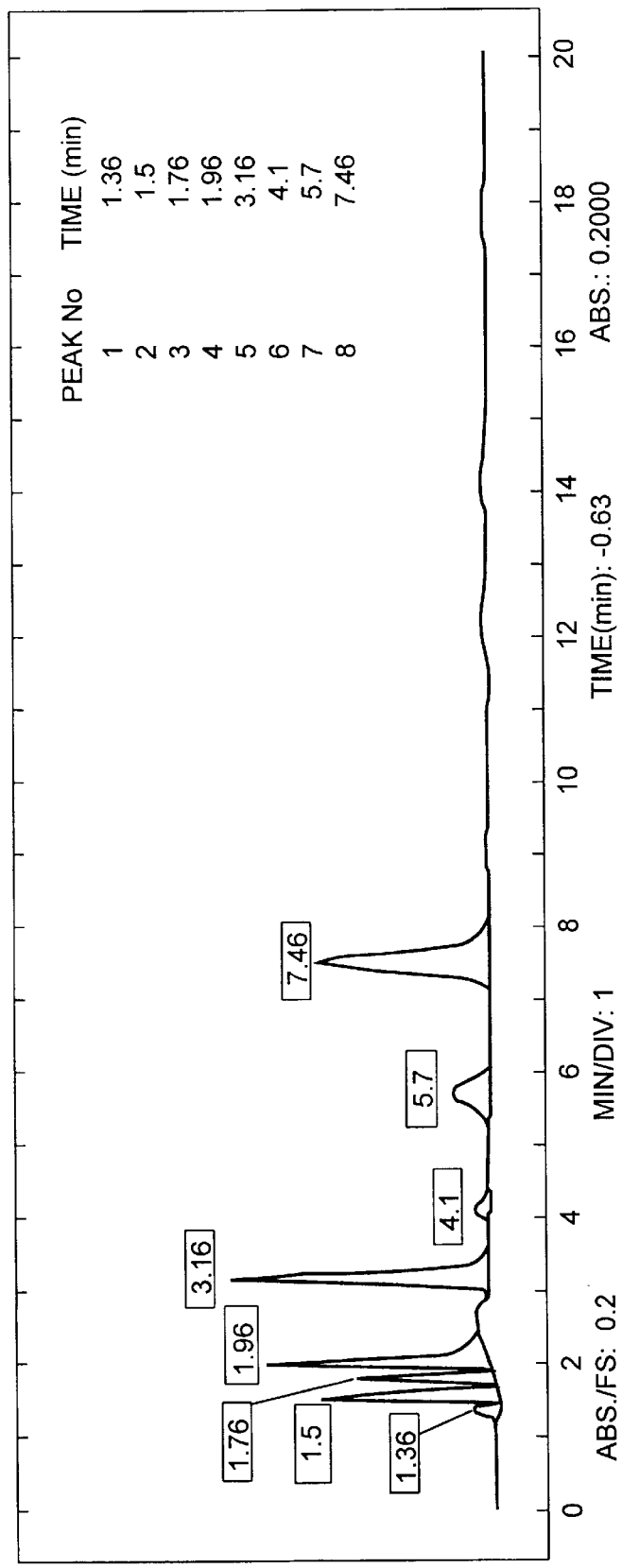

FIG. 1 relates to TLC chromatograph of Rheum emodi detected under UV-at 254 nm;

FIG. 2 relates to TLC chromatograph of Rheum emodi detected under UV-at 366 nm;

FIG. 3 relates to HPLC chromatograph of Rheum emodi;

FIG. 4 relates to TLC chromatograph of Phyllanthus amarus detected under UV-at 254 nm;

FIG. 5 relates to HPLC chromatograph of Phyllanthus amarus detected under UV-at 254 nm;

FIG. 6 relates to TLC chromatograph of Eclipta alba detected under UV-at 254 nm;

FIG. 7 relates to TLC chromatograph of Eclipta alba detected under UV-at 366 mn;

FIG. 8 relates to TLC chromatograph of Andrographis paniculata detected under UV-at 254 nm;

FIG. 9 relates to HPLC chromatograph of Andrographis paniculata detected under UV-at 254 nm;

FIG. 10 relates to TLC chromatograph of Picrorrhiza kurroa detected under UV-at 254 nm;

FIG. 11 relates to HPLC chromatograph of Picrorrhiza kurroa detected under UV-at 254 nm;

FIG. 12 relates to TLC chromatograph of polyherbal extracts syrup detected under UV-at 254 nm;

FIG. 13 relates to TLC chromatograph of polyherbal extracts syrup detected under UV-at 366 nm;

FIG. 14 relates to TLC chromatograph of polyherbal extracts syrup, extracts & marker compounds detected under UV-at 254 nm;

FIG. 15 relates to TLC chromatograph of polyherbal extracts syrup, extracts & marker compounds detected under UV-at 366 nm;

FIG. 16 relates to HPLC chromatograph of polyherbal extract syrup containing Eclipta alba, Phyllanthus amarus, Picrorrhiza kurroa, Andrographis paniculata and Rheum emodi detected under UV-at 254 nm;

FIGS. 17–24 are Micro-Photographs of the Liver histopathology hepatoprotection provided by Polyherbal pharmaceutical preparation in experimental acute hepatoxicity models.

Figure 17:
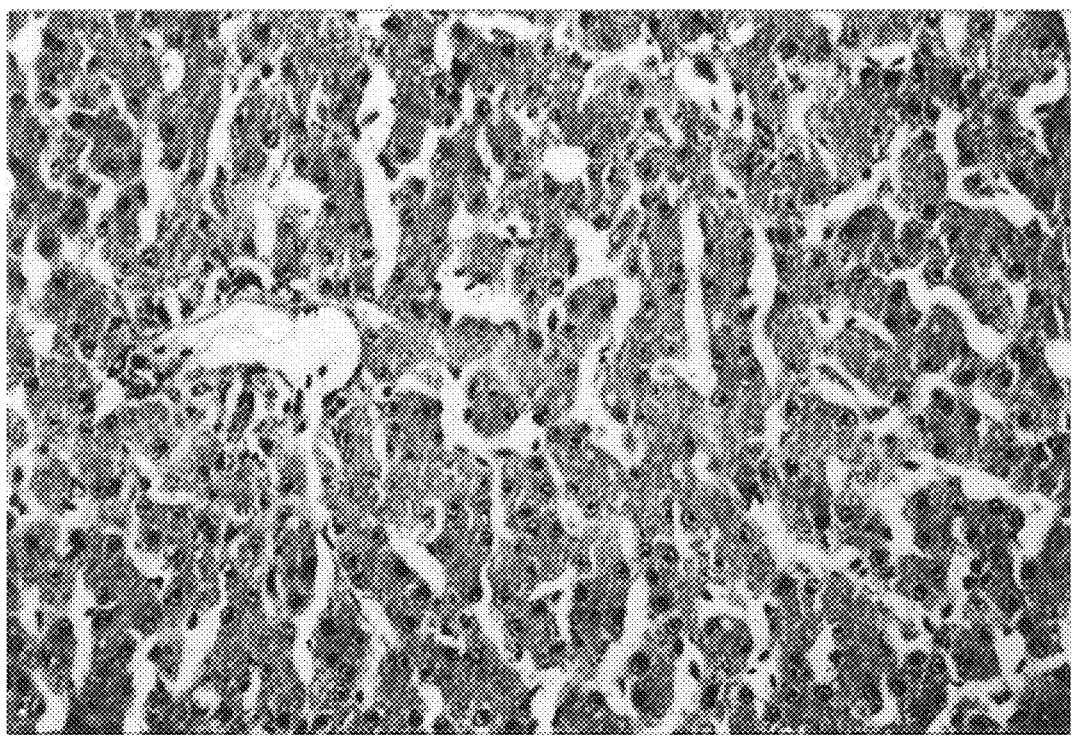

FIG. 17 shows hepatocytes which are polyherbal pharmaceutical preparation (without *Rhuem emodi* Wall) protected and galactosamine challenged and shows that the hepatocytes are well preserved and arranged in well defined cell plates. In the center a portal tract is also present. The overall architecture of the liver parenchyma has been restored to normal. Hematoxylin & Esoin (Original magnification×100).

Figure 18:
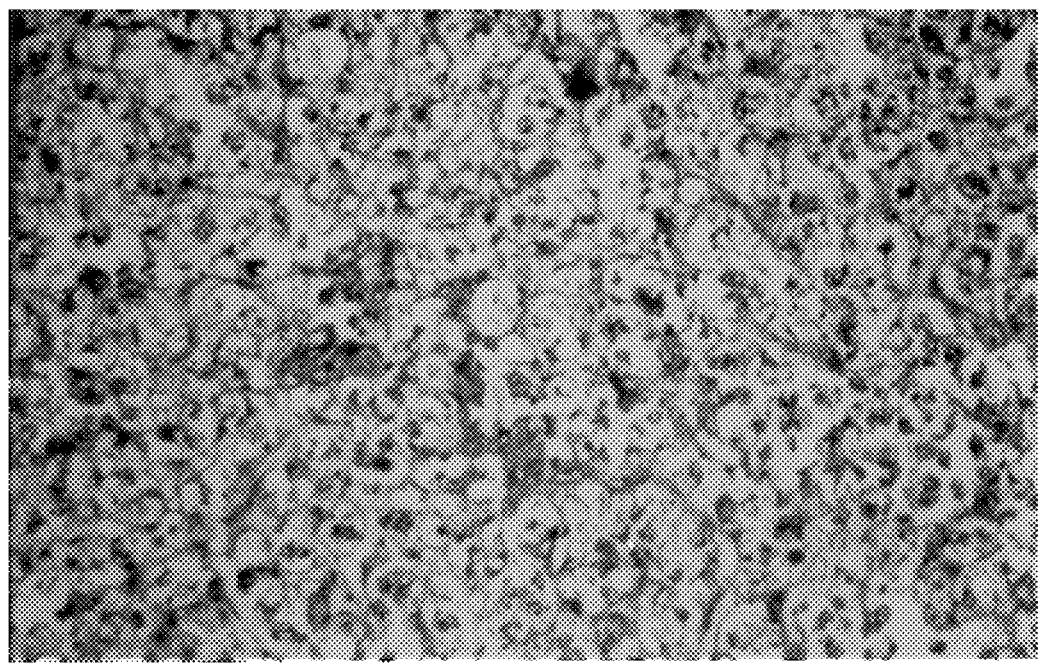

FIG. 18 shows a marked lobular disarray of the hepatocytes treated with saline and galactosamine(control) and shows marked lobular disarray of the hepatocytes. There is degeneration, ballooning of the hepatocytes, along with necrosis. Foci of bile ductular proliferation are also present. Hematoxylin & Esoin (Original magnification×100).

Figure 19:
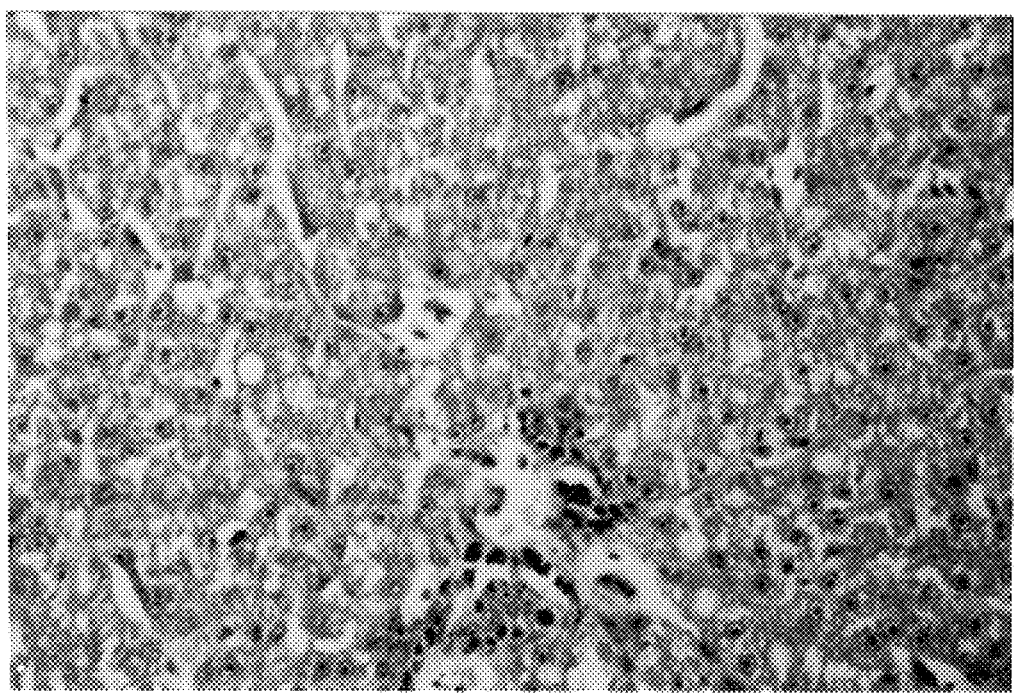

FIG. 19 shows the liver which is protected by polyherbal preparation (without *Rheum emodi* Wall) and challenged by thioacetamide and shows that liver parenchyma is restored normal except for the presence of fat vacuoles in the hepatocyte in some focal areas. The portal tract is preserved. Hematoxylin & Esoin (Original magnification×100).

Figure 20:
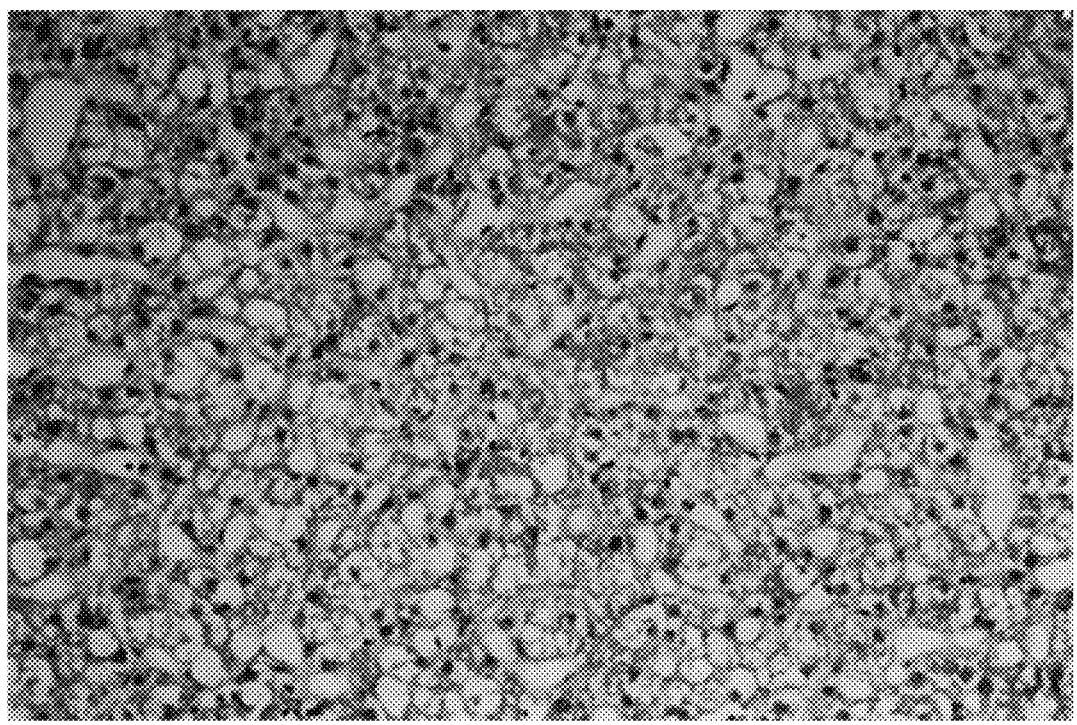

FIG. 20 shows the hepatocytes which are treated with saline and challenged with thioacetamide(control) and shows a diffuse and marked hepatocyte changes which are characterized by necrosis, cytoplasmic degeneration, and ballooning of cells. Some of the hepatocytes also show fatty change. Hematoxylin & Esoin (Original magnification× 100).

Figure 21:
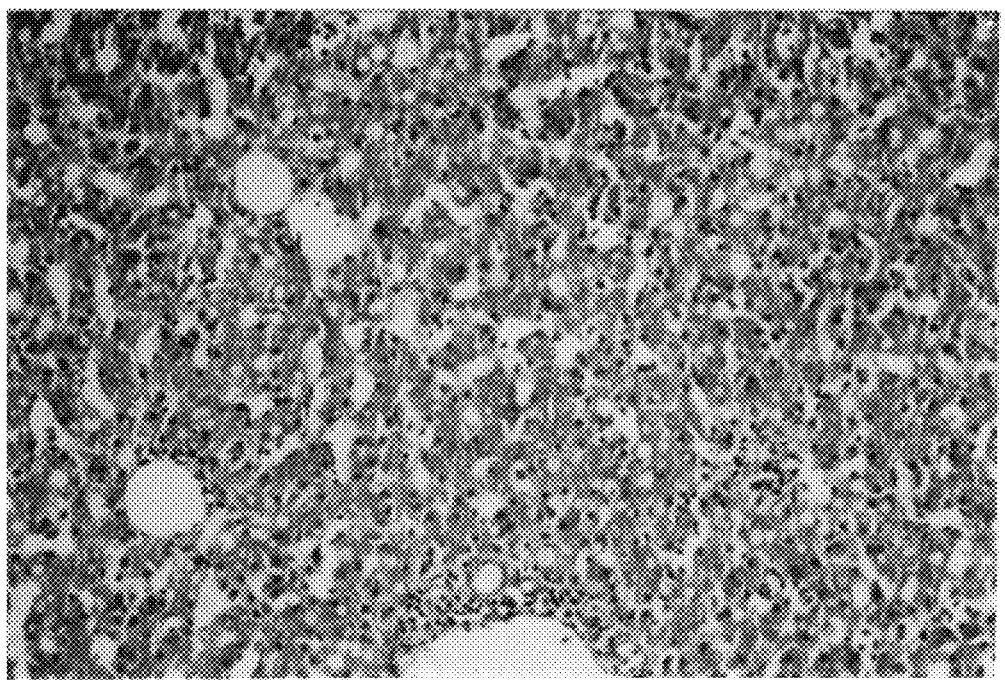

FIG. 21 shows the architecture of the liver which is protected by polyherbal composition (without *Rheum emodi* Wall) and challenged by aflatoxin (AFB1) and shows that the lobular architecture of the liver is preserved and the hepatocytes are arranged in well defined cell plates. Focal areas of hepatocytes fatty change is present. The bile ductular proliferation as observed in the control group (refer to polyherbal pharmaceutical preparation unprotected FIG. 20) is absent. Hematoxylin & Esoin (Original magnification× 100).

Figure 22:
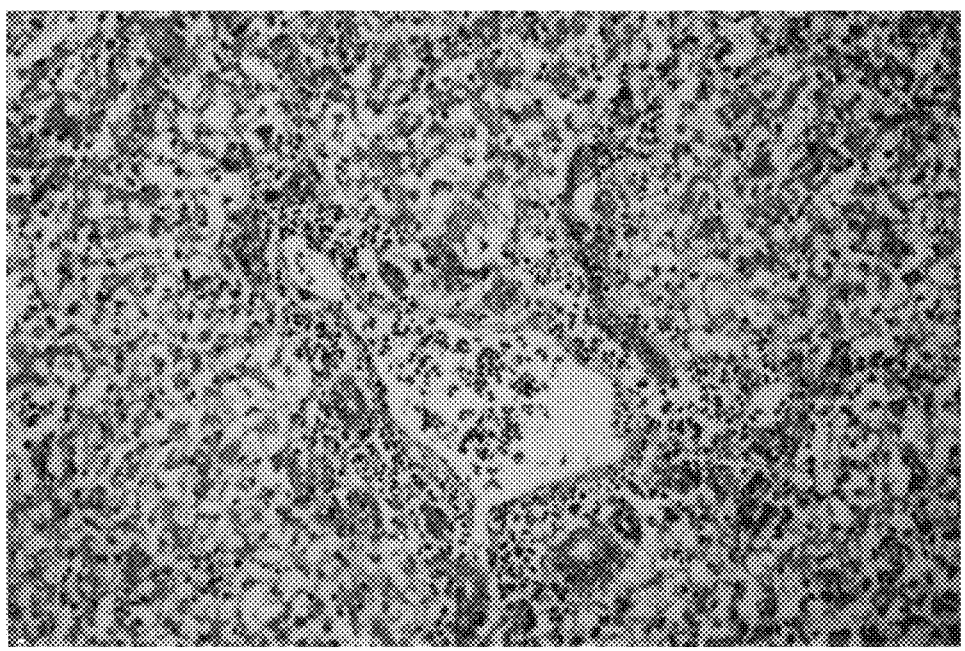

FIG. 22 shows the hepatocytes treated with saline and challenged with aflatoxin(AFB1)(control) and shows a diffuse hepatocyte changes characterized by cytoplasmic degeneration, necrosis, and ballooning of the cells. In the center a protal tract is present which shows proliferation of bile ductules accompanied by infiltration by mononuclear inflammatory cells. Hematoxylin & Esoin (Original magnification×100).

Figure 23:
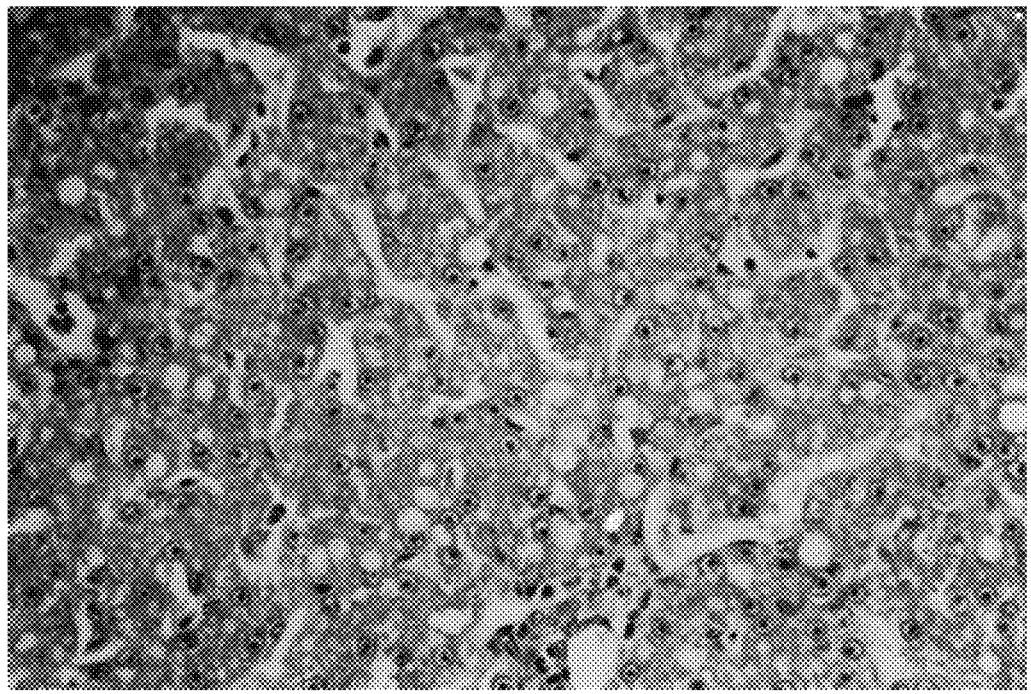

FIG. 23 shows the lobular architecture of the liver which is polyherbal preparation (without *Rheum emodi* Wall) protected, and rifampicin and isoniazid challenged and shows that the lobular architecture of the liver has been restored to normal. The hepatocytes are arranged in well defined cell plates. Only a few hepatocytes show fat vacuoles in their cytoplasm. Hematoxylin & Esoin (Original magnification×100).

Figure 24:
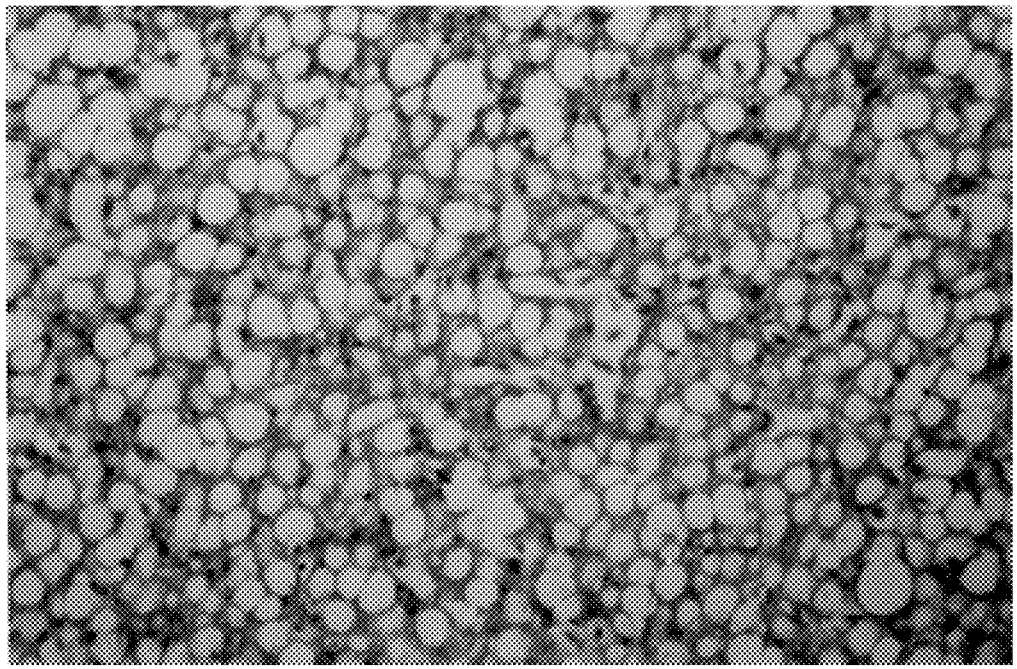

FIG. 24 shows the hepatocytes treated with saline and challenged by rifampicin and isoniazid(control) and shows diffuse marked macrovesicular type fatty change in the hepatocytes, the fat vacoules have completely replaced the cell cytoplasm in some areas. Hematoxylin & Esoin (Original magnification×100).

Each of the herbal extracts obtained from the specific herb employed in the present invention is authenticated. The applicant has taken pains to test and provide identification of each of the herbal extract as well as the polyherbal extracts. The analytical standardisation and the finger print profile of each of the essential herbs and their combination are given below:

Finger Print Profile of the REVAND CHINI (*Rheum emodi* Wall)

Rhubarb roots of Revand chini (*Rheum emodi* Wall.) are used here. It contains Chrysophanic acid, an allied substance "EMODIN", a glucoside Rhaponticin, a Tannin named Rheotannic acid. A method of finger print by Fhin Layer Chromatography (TLC) and High performance liquid chromatography (HPLC) method were developed.

THIN LAYER CHROMATOGRAPHY (TLC)

Using a silica gel F254 precoated plates (Merck silica gel 60 F254 are suitable) and a mixture of 50 volume of ethyl acetate, 7 volume of Fornic acid, 3 volume of Glacial acetic acid, 3 volume of ethyl methyl ketone, 10 volume of water as the mobile phase. Apply separately to the plate 10 μl of the following solutions.

For solution (1) of extract, separately weigh about 1 gm of extract in a beaker, add 25 ml of ethyl acetate shake for about 30 minutes and filter. After removal of the plate, allow it to dry in air and examine under ultraviolet light at 254 nm and 366 nm.

OBSERVATIONS: In UV 254 nm (TLC chromatogram photograph No. 1, accompanying the specification) orange, yellow and some other zones are visible. The broad zone in the upper Rf (at about 0.56) represents mixture of glycosides of emodin and chrysophanic acid. In 399 nm (TLC chromatogram photograph No. 2 accompanying the specification) some aglycones migrate with the solvent front to an Rf at about 0.80 and some other zones also appear in the lower Rf range of 0.36–0.42.

HIGH PERFORMANCE LIQUID CHROMATOGRAPHY (HPLC)

Using the following solution (1) weigh about 1 gm of sample in a beaker, add 20 ml of mobile phase warm, shake and filter. The chromatographic procedure carried out using (a) A stainless steel column ODS (C18) (300 mm×4.6 mm), (b) a mixture of 50 volume of 0.1% of v/v of orthophosphoric acid and 50 volume of methanol as mobile phase with a flow rate 1 ml per minute and (c) detection wavelength of 254 nm.

OBSERVATIONS: There (HPLC chromatogram, FIG. No. 3 accompanying the specifications) are about 10 components which are separated out. These are in different concentrations. These components are correlated to the components of reference extract. These components are most probably aglycones and one of them in chrysophanic acid.

Finger Print Profile of the BHUMYAMALAKI (*Phyllanthus amarus* Linn.):

Whole plant of BHUMYAMALAKI (*Phyllanthus amarus* Linn.) can be used here. It contains Phyllanthin (Bitter and Hypophyllanthin Non bitter). A method of finger print by Thin Layer Chromatography (TLC) and High performance liquid chromatography (HPLC) methods were developed.

THIN LAYER CHROMATOGRAPHY (TLC)

Using a silarised silica gel F254 precoated plates (Merck silica gel 60 F254 are suitable) and a mixture of 80 volume of benzene and 20 volume of ethyl acetate as the mobile phase. Apply separately to the plate 10 μl of the following solutions. For solution (I) of extract, weigh about 1 gm of sample in a beaker, add 20 ml of diethyl ether, warm, shake and filter. After removal of the plate, allow it to dry in air and examine under ultraviolet light at 254 nm and 366 nm.

OBSERVATIONS: In UV 254 nm (TLC chromatogram photograph No. 4 enclosed with the specification) there are two zones in the Rf range observed. In the lower zone at about Rf 0.25 represents Phyllanthin.

HIGH PERFORMANCE LIQUID CHROMATOGRAPHY (HPLC)

Using the following solution (1) weigh about 1 gm of sample in a beaker, add 20 ml of mobile phase, waim, shake and filter. For solution (2) weight about 0.01 gm of reference standard in a beaker, add 20 nm of methanol, shake to mix and dilute to 100 ml with methanol. The chromatographic procedure carried out using (a) A stainless steel column ODS (C18) (300 mm×4.6 mm), (b) A mixture of 50 volume of 0.1% v/v of orthophosphoric acid and 50 volume of methanol as mobile phase with a flow rate 1 ml per minute and (c) detection wave length of 254 nm.

OBSERVATIONS: There (HPLC chromatogram, FIG. No. 5 accompanying the specification) are some components eluted. These components are correlated to the components of reference extract.

Finger Print Profile of the BHRINGRAJ (*Eclipta alba* Hassk.):

Whole plant of BHRINGRAJ (*Eclipta alba* Hassk.) is taken here. It contains an alkaloid Ecliptine and resin. A method of finger print by Thin Layer Chromatography (TLC) method was developed.

THIN LAYER CHROMATOGRAPHY (TLC)

Using a silica gel F254 precoated plates (Merck silica gel 60 F254 are suitable) and a mixture of 70 volume of ethyl acetate, 15 volume of methanol, 6 volune of ethyl methyl ketone, 10 volume of water as the mobile phase. Apply separately to the plate 10 μl of the following solutions. For solution (1) of extract, weigh about 1 gm of sample in a beaker, add 20 ml of methanol, 0.5 ml of ammonia solution, warm, shake and filter. After removal of the plate, allow it to dry in air and examine under ultraviolet light at 254 nm and 366 nm.

OBSERVATIONS: In UV 254 nm (TLC chromatogram photograph No. 6 enclosed with the specification) few zones are visible. The lower Rf range at about 0.25 a very light zone of an alkaloid (Ecliptin) is present. In UV 366 nm (TLC chromatogram photograph No. 7) red and blue fluorescent zones are distributed over the whole Rf range starting from 0.10 and spreading over between 0.46–0.75.

Finger Print Profile of the KALMEGH (*Andrographis paniculate* Nees):

Whole plant of KALMEGH (*Andrographis paniculate* Nees.) is used here. It contains Andrographolides. A method of finger print by Thin Layer Chromatography (TLC) and High performance liquid chromatography (HPLC) method were developed.

THIN LAYER CHROMATOGRAPHY (TLC)

Using a silica gel F254 precoated plates (Merck silica gel 60 F254 are suitable) and a mixture of 50 volume of ethyl acetate, 7 volume of Formic acid, 3 volume of Glacial acetic acid, 3 volume of ethyl methyl ketone, 10 volume of water as the mobile phase. Apply separately to the plate 10 μl of the following solutions. For solution (1) of extract, weigh about 1 gm of sample in a beaker, add 20 ml of methanol, warm, shake and filter. For solution (2) weigh about 0.01 gm of Andrographolide reference standard in a beaker, add 20 nm of methanol, shake to mix and dilute to 100 ml with methanol. After removal of the plate, allow it to dry in air and examine under ultraviolet light at 254 nm and 366 nm.

OBSERVATIONS: In UV 254 nm (TLC chromatogram photograph No. 8 enclosed with the specification) there are some zones in the upper Rf range. At Rf about 0.66 a zone represents an andrographolide.

HIGH PERFORMANCE LIQUID CHROMATOGRAPHY (HPLC)

Using the following solution (1) weigh about 1 gm of sample in a beaker, add 20 ml of mobile phase warm, shake and filter. For solution (2) weigh about 0.01 gm of Andrographolide reference standard in a beaker, add 20 ml of methanol, shake to mix and dilute to 100 ml with methanol, the chromatographic procedure carried out using (a) A stainless steel column ODS (C18) (300 mm×4.6 mm), (b) A mixture of 50 volume of 0.1% v/.v of orthophosphoric acid and 50 volume of methanol mobile phase with a flow rate 1 ml per minute and (c) detection wavelength of 254 nm.

OBSERVATIONS: There (HPLC chromatogram, FIG. No. 9 of the accompanying drawings) is only one component which eluted. This component is an Andrographolide.

Finger Print Profile of KUTKI (*Picrorrhiza kurroa* Royle ex Benth.):

Rhizomes of KUTKI (*Picrorrhiza kurroa* Royle ex Benth.) are used here. It contains Glucoside viz. Picroside Kutkoside. A method of finger print by Thin Layer Chromatography (TLC) and High performance liquid chromatography (HPLC) method were developed.

THIN LAYER CHROMATOGRAPHY (TLC)

Using a silica gel F254 precoated plates (Merck silica gel 60 F 254 are suitable) and a mixture of 50 volume of ethyl acetate, 7 volume of Formic acid, 3 volume of Glacial acetic acid, 3 volume of ethyl methyl ketone, 10 volume of water as the mobile phase. Apply separately to the plate 10 µl of the following solutions. For solution (1) of extract, weigh about 1 gm of sample in a beaker. add 20 ml of methanol, warm, shake and filter. After removal of the plate, allow it to dry in air and examine under ultraviolet light at 254 nm and 366 nm.

OBSERVATIONS: In UV 254 nm (TLC chromatogram photograph No. 10, enclosed with the specification) two zones are visible. The upper zone at Rf about 0.49 represents picroside. The lower zone at Rf about 0.40 represents kutkoside.

HIGH PERFORMANCE LIQUID CHROMATOGRAPHY (HPLC)

Using the following solution (1) weigh about 1 gm of sample in a beaker, add 20 ml of mobile phase, warm and shake. The chromatographic procedure was carried out using (a) A stainless steel column ODS (C 18) (300 mm×4.6 mm), (b) a mixture of 50 volume of 0.1% of V/V of orthophosphoric acid and 50 volume of methanol as mobile phase with a flow rate of 1 ml per minute and (c) detection wavelength of 254 nm.

OBSERVATIONS: There (HPLC chromatogram, FIG. No. 11 enclosed with specifications) are numerous components which eluted these are present in different concentrations. These components are correlated to the components of reference extract. One of these is Picroside and the other is Kutkoside.

Finger Print Profile of the POLYHERBAL Extracts Syrup

Polyherbal extract syrup contains water extract of the BHRINGRAJ (*Eclipta alba* Hassk.), BHUMYAMALAK (*Phyllanthus amarus* Linn.), KUTKI (*Picrorrhiza kurroa* Royle ex Benth.), KALMEGH (*Andrographis paniculate* Nees.), REVAND CHINI (*Rheum emodi* Wall.). Active constituents of BHRINGRAJ (*Eclipta alba* Hassk.)—An alkaloid ECLIPTIN BHUMYAMALAKI (*Phyllanthus amarus* Linn.)—Phyllanthin, KUTKI (*Picrorrhiza kurroa* Royle ex Benth.)—Picrosides and Kutkosides KALMEGH (*Andrographis paniculate* Nees.)—Andrographolides, REVAND CHINI (*Rheum emodi* Wall.)—Chrysophani acid. A method of finger print by Thin Layer Chromatography (TLC) and High performance liquid chromatography (HPLC) were developed.

THIN LAYER CHROMATOGRAPHY (TLC)

Using a silica gel F254 precoated plates (Merck silica gel 60 F254 are suitable) and a mixture of 50 volume of ethyl acetate, 7 volume of Formic acid, 3 volume of glacial acetic acid, 3 volume of ethyl methyl ketone, 10 volume of water as the mobile phase.

Apply separately to the plate 10 µl of the following solutions, for solution (1) shake 10 ml of the sample being examined with 10 ml of ethyl acetate for 15 minutes, use the ethyl acetate layer. For solution (2), (3), (4), (5). (6), (7) of extracts, separately weigh about 1 gm of each extract in separate beaker, add 25 ml of ethyl acetate, shake for about 30 minutes and filter. After removal of the plate, allow it to dry in air and examine under ultraviolet light at 254 nm and 366 nm.

OBSERVATIONS: In UV 254 nm (TLC chromatogram photograph Nos. 12. 13, 14 & 15, enclosed with the specifications), numerous zones are visible. In UV 366 nm orange-red, blue and yellow fluorescent zones are distributed over the whole Rf range. The Rf of most zones in the present polyherbal composition tracks can be correlated to the Rf of the corresponding zones found in the tracts of marker compounds and reference extracts respectively. The Rf of the different components in the developed tracks are found to be at about the following values: Kutkin (Rf 0.40 Kutkoside, Rf 0.49 Picroside); Andrographolide (Rf 0.66); *Rheum emodi* Wall. (Rf 0.56). The zone probably represents a mixture of glucosides of emodin and chrysophani acid, Rf 0.80 whereby aglycones migrate as an orange-red zone at the solvent front; *Eclipta alba*(Rf 0.25 Ecliptin) and *Phyllanthus* (Rf 0.25 Phyllanthin).

HIGH PERFORMANCE LIQUID CHROMATOGRAPHY (HPLC)

Using the following solution (1) measure 10 ml of sample being examined in a 50 ml volumetric flask and dilute upto mark with mobile phase. The chromatographic procedure carried out using (a) A stainless steel column ODS (C18) (300 mm×4.6 mm), (b) A mixture of 50 volume of 0.1% V/V of orthophosphoric acid and 50 volume of methanol as mobile phase with a flow rate of 1 ml per minute and (c) detection wavelength of 254 nm.

OBSERVATIONS: There (HPLC chromatogram, FIG. No. 16 enclosed with specifications) are some components eluted, which correlated to the components of reference extracts. This component is an Andrographolide.

EXAMPLE 2

Describes the Clinical efficacy of the present polyherbal pharmaceutical composition (with *Rheum emodi*) in the treatment of acute viral hepatitis caused by Hepatitis E virus infection

MATERIAL & METHOD

Ten (10) patients (8 males, 2 females) of a mean age of 18.5 years (range 18 to 45 years) presenting within one week of the onset of the clinical symptoms suggestive of classical acute viral hepatitis (AVH) were included in the study.

The diagnosis of AVH was established by the clinical symptoms (acute onset of jaundice, gastrointestinal symptoms e.g. abdominal pain, anorexia, vomiting along with tender hepatomegaly: Sherlock & Dooley, 1993).

The diagnosis was supplemented by abnormal liver function tests e.g. estimation of Serum Bilirubin, ALT (SGPT), AST (SGOT), and Alkaline Phosphatase (Bayer Diagnostics, Baroda, India). The diagnosis of the etiological agents (hepatitis viruses A, B, C, D and E) were done by the following parameters: hepatitis B virus—presence of HBc IgM with or without HBsAg, hepatitis A virus—presence of HAV IgM, hepatitis C virus—presence of anti HCV, hepatitis D virus—presence of anti HDV IgM (All from Sorin Biomedica), hepatitis E virus—presence of anti HEV IgM and IgG (Gene Labs. Diagnostics PTE Ltd., Singapore). All the serological tests were done by Enzyme Immune Assay (ELISA) at the time of clinical presentation and the subsequent intervals during therapy.

In all the 10 patients the serological markers of hepatitis A, B, C and D were absent and only anti HEV IgM with or without IgG was present. Further in all the 10 patients, the other possible causes which might have led to a similar clinical presentation e.g. surgical jaundice, drug induced cholestasis, herpes and cytomegalo virus infection were also excluded.

A study was conducted as per the guidelines on WHO Medical Research on human beings. Therefore, a prior consent of all the patients were obtained and they were explained about the treatment protocol and investigations. The preparation of polyhedral pharmaceutical composition in the tablet form for clinical use in the above 10 patients has been described in example 1.

Each patient was given 2 tablets of polyherbal pharmaceutical composition, two times a day for a period of 4 weeks. The clinical assessment and the liver function tests along with the anti HEV IgM and IgG was done at two weekly intervals, also if required at weekly interval (as in two patients No. 104 and 110 results shown as separate tables).

RESULTS

The results demonstrating the efficacy of polyherbal pharmaceutical composition on the improvement of clinical signs and symptoms of the patients of acute E virus hepatitis have been shown in Table 1. In majority of the patients there was a complete improvement in anorexia, loss of appetite, abdominal discomfort, lethargy and nausea 2 weeks after therapy with polyherbal pharmaceutical composition. At the end of 4 weeks there was a complete clinical recovery in all the 10 patients.

Table 2 summarises the mean of biochemical tests at the time of presentation and at the end of 4 weeks treatment with polyherbal pharmaceutical composition. Table 3, 4, 5, 6 gives the details of each liver function test parameters e.g. serum bilirubin, ALT (SGPT), AST (SGOT), Alkaline phosphatase of the individual patients (No. 101 to 110) along with the mean values at the time of clinical presentation, and at 2 and 4 weeks interval during the therapy with polyherbal pharmaceutical composition. A marked improvement in the above biochemical parameters were observed at the end of 2 weeks therapy, with a complete recovery at the end of 4 weeks therapy in all the 10 patients, thereby demonstrating the efficacy of polyherbal pharmaceutical composition in the treatment of acute E virus hepatitis.

The above observations of improvement in the liver function tests are further elucidated by Table No. 7, 8 showing details of the liver function tests in the two patients (No. 104, 110) done at weekly intervals during polyherbal pharmaceutical composition therapy. A significant improvement was noted in both the patients as early as 1 week of receiving the therapy.

Table No. 9 shows the presence of anti HEV IgM and IgG antibody in all the 10 patients at the time of presentation and at 2 weekly interval during therapy with polyherbal pharmaceutical composition. All the 10 patients were positive for anti HEV IgM at the time of clinical presentation and at 2 weeks interval. At 4 weeks, anti HEV IgM was detected in only 2 out of 10 patients (No. 108 and 109). However, anti HEV-IgG persisted in all the ten patients.

TABLE 1 demonstrates the effects on physical sign and symptoms of the patients of classical Acute E virus hepatitis receiving polyherbal pharmaceutical composition therapy (10 patients)

| Observations | Initial | 2 weeks | 4 weeks |
|---|---|---|---|
| General well being | ++ | + | − |
| Anorexia | +++ | − | − |
| Loss of appetite | +++ | − | − |
| Abdominal discomfort | +++ | − | − |
| Feeling of lethargy | +++ | − | − |
| Nausea | ++++ | − | − |
| Jaundice | ++++ | + | − |
| Hepatomegaly | ++++ | + | − |

+ = Mild; ++ = Moderate; +++ = Severe; ++++ = Extremely severe; − = Absent

TABLE 2

Summary of Liver Function Tests (mean values shown) from the patients of acute E virus hepatitis receiving the Polyherbal Pharmaceutical composition

| No. of patients | ALT (IU/L) | | AST (IU/L) | | S. Bilirubin (mg/dl) | | Alkaline Phosphatase (IU/L) | |
|---|---|---|---|---|---|---|---|---|
| | Initial | After treatment | Initial | After treatment | Initial | After treatment | Initial | After treatment |
| 10 | 1836.30 | 31.50 | 1472.30 | 31 | 5.01 | 0.86 | 388.20 | 122.90 |

Normal values: ALT (SGOT) 10–35 IU/L AST (SGPT) = 10–49 IU/L
S. Bilirubin = 0.3–1.0 mg/dl, Alk. Phosphatase = 60–170 IU/L

TABLE 3

Polyherbal pharmaceutical composition efficacy in acute E virus hepatitis shows the values of Serum Bilirubin prior to therapy and at subsequent intervals in patients

| | Polyherbal Pharmaceutical Composition Therapy | | |
|---|---|---|---|
| Patient S. No. | Initial | 2 weeks | 4 weeks |
| 101 | 8.67 | 2.37 | 1.0 |
| 102 | 1.56 | 1.29 | 0.90 |
| 103 | 3.39 | 1.62 | 0.81 |
| 104 | 2.11 | 1.53 | 0.99 |
| 105 | 5.46 | 1.72 | 0.71 |
| 106 | 6.85 | 1.61 | 1.00 |
| 107 | 5.68 | 1.73 | 1.00 |
| 108 | 6.27 | 1.61 | 0.58 |
| 109 | 7.73 | 3.67 | 0.92 |
| 110 | 2.46 | 1.29 | 0.78 |
| Mean values | 5.01 | 1.84 | 0.86 |

Normal values: Serum Bilirubin = 0.3 to 1.0 mg/dL

TABLE 4

Polyherbal pharmaceutical composition efficacy in acute hepatitis E virus shows the values of Serum ALT (SGPT) prior to therapy and at subsequent intervals in patients

| | Polyherbal Pharmaceutical Composition Therapy | | |
|---|---|---|---|
| Patient S. No. | Initial | 2 weeks | 4 weeks |
| 101 | 1795 | 137 | 30 |
| 102 | 67 | 36 | 34 |

TABLE 4-continued

Polyherbal pharmaceutical composition efficacy in acute hepatitis E virus shows the values of Serum ALT (SGPT) prior to therapy and at subsequent intervals in patients

| Patient S. No. | Polyherbal Pharmaceutical Composition Therapy | | |
|---|---|---|---|
| | Initial | 2 weeks | 4 weeks |
| 103 | 375 | 156 | 28 |
| 104 | 2830 | 521 | 36 |
| 105 | 1910 | 68 | 21 |
| 106 | 2720 | 48 | 32 |
| 107 | 2607 | 85 | 31 |
| 108 | 2725 | 178 | 32 |
| 109 | 1659 | 118 | 36 |
| 110 | 1675 | 39 | 35 |
| Mean values | 1836.30 | 138.60 | 31.50 |

Normal values: Serum ALT (SGPT) = 10 to 35 IU/L

TABLE 5

Polyherbal pharmaceutical composition efficacy in acute hepatitis E virus shows the values of Serum AST (SGOT) prior to therapy and at subsequent intervals in patients

| Patient S. No. | Polyherbal Pharmaceutical Composition Therapy | | |
|---|---|---|---|
| | Initial | 2 weeks | 4 weeks |
| 101 | 1405 | 91 | 28 |
| 102 | 61 | 36 | 30 |
| 103 | 132 | 38 | 27 |
| 104 | 2735 | 267 | 32 |
| 105 | 1330 | 45 | 26 |
| 106 | 2310 | 50 | 34 |
| 107 | 2182 | 62 | 32 |
| 108 | 1631 | 83 | 31 |
| 109 | 1585 | 58 | 37 |
| 110 | 1352 | 40 | 33 |
| Mean values | 1472.30 | 77 | 31 |

Normal values: Serum AST (SGOT) = 10 to 40 IU/L

TABLE 6

Polyherbal pharmaceutical composition efficacy in acute hepatitis E virus shows the values. of Serum Alkaline Phosphatase prior to therapy and at subsequent intervals in patients

| Patient S. No. | Polyherbal Pharmaceutical Composition Therapy | | |
|---|---|---|---|
| | Initial | 2 weeks | 4 weeks |
| 101 | 568 | 237 | 125 |
| 102 | 257 | 142 | 136 |
| 103 | 387 | 146 | 120 |
| 104 | 441 | 241 | 168 |
| 105 | 404 | 169 | 112 |
| 106 | 253 | 140 | 104 |
| 107 | 689 | 425 | 120 |
| 108 | 266 | 97 | 112 |
| 109 | 354 | 136 | 120 |
| 110 | 263 | 167 | 112 |
| Mean values | 388.20 | 190 | 122.90 |

Normal values: Serum Alkaline Phosphatase = 60 to 170 IU/L

TABLE 7

Patient No. 104: Polyherbal Pharmaceutical Composition efficacy in acute hepatitis E virus infection: shows the finding of liver function test, anti-HEV IgM and IgG at weekly intervals

| Parameter | Polyherbal pharmaceutical Composition Therapy (weeks) | | | |
|---|---|---|---|---|
| | Initial | 2 wk | 3 wk | 4 wk |
| Serum Bilirubin | 2.11 | 1.53 | 0.99 | 0.76 |
| ALT (SGPT) | 2830 | 521 | 49 | 36 |
| AST (SGOT) | 2735 | 267 | 44 | 32 |
| Alkaline Phosphatase | 441 | 427 | 344 | 168 |
| Anti HEV IgM | + | + | − | − |
| Anti HBV-IgG | − | + | + | + |

Normal values: AST = 10–35 IU/L; ALT = 10–30 IU/ml
S. Bilirubin = 0.3–1.0 mg/dl; Alk. phosphatase = 60–170 IU/L
+ = Positive; − = Negative

TABLE 8

Patient No. 110: Polyherbal Pharmaceutical Composition efficacy in acute hepatitis E virus infection: shows the finding of liver function test, anti-HEV IgM and IgG at weekly intervals

| Parameter | Polyherbal pharmaceutical Composition Therapy (weeks) | | | | |
|---|---|---|---|---|---|
| | Initial | 1 wk | 2 wk | 3 wk | 4 wk |
| Serum Bilirubin | 2.46 | 1.29 | 1.02 | 0.75 | 0.78 |
| ALT (SGPT) | 1675 | 276 | 39 | 36 | 35 |
| AST (SGOT) | 1352 | 71 | 40 | 33 | 32 |
| Alkaline Phosphatase | 263 | 196 | 167 | 123 | 112 |
| Anti HEV IgM | + | + | + | − | − |
| Anti HBV IgG | − | + | + | + | + |

Normal values: AST = 10–35 IU/L; ALT = 10–30 IU/ml;
S. Bilirubin = 0.3–1.0 mg/dl; Alk. phosphatase = 60–170 IU/L;
+ = Positive; − = Negative

TABLE 9

Polyherbal pharmaceutical composition efficacy in acute E virus hepatitis shows the presence of Anti HEV IgM and IgG prior to therapy and at subsequent intervals in patients

| | Polyherbal Pharmaceutical Composition Therapy | | | | | |
|---|---|---|---|---|---|---|
| | Initial | | 2 weeks | | 4 weeks | |
| | Anti HEV | | Anti HEV | | Anti HEV | |
| Patient S. No. | IgM | IgG | IgM | IgG | IgM | IgG |
| 101 | + | + | + | + | − | + |
| 102 | + | + | + | + | − | + |
| 103 | + | + | + | + | − | + |
| 104 | + | + | + | + | − | + |
| 105 | + | + | + | + | − | + |
| 106 | + | + | − | + | − | + |
| 107 | + | − | + | + | − | + |
| 108 | + | + | + | + | + | + |
| 109 | + | + | + | + | + | + |
| 110 | + | − | + | + | − | + |

+ = Positive; − = Negative

The present polyherbal pharmaceutical composition thus promotes a rapid rate of clinical recovery in subjective symptoms and objective parameters supported by biochemical liver function tests and HEV antibody responses in patients of acute Hepatitis E virus infection thereby demonstrating that there is a gross reduction in the morbidity period of the disease and a rapid recovery.

Method of Treatment of Acute Hepatitis E Virus (HEV) Infection:

The treatment relates to acute Hepatitis E virus infection in form of a daily dose of 0.5 to 6 gm daily of present polyherbal pharmaceutical composition in divided doses which can be administered orally for a period of about 4 to 12 weeks approximately.

EXAMPLE 3

The efficacy of the present polyherbal pharmaceutical composition in the healthy of hepatitis B virus carrier who developed a super imposed acute hepatitis E virus infection: has been illustrated as below by demonstrating the efficacy of polyherbal pharmaceutical composition in two healthy hepatitis B carriers developing acute Hepatitis E virus infection.

Patient No. 111: A 45 year healthy male who has been a chronic carrier of hepatitis B virus (as demonstrated by the persistence of HBsAg at two different intervals of 3 months each, Anti HBc IgM=Negative, Serum Bilirubin 1.21 mg/dL, ALT=46 IU/L, AST=39 IU/L, Alkaline Phosphatase=118 IU/L, mean values) without any clinical symptoms of a liver disease or a past history of jaundice developed acute hepatitis E virus infection (Anti HEV IgM positive) thereby presenting as acute viral hepatitis.

The Table 10 shows the details of the liver function tests at the time of presentation as acute viral Hepatitis (before the start of therapy) and subsequently upto 16 weeks at the interval of 4 weeks during therapy with polyherbal pharmaceutical compositions.

He received the polyherbal pharmaceutical composition in the doses of two tablets (preparation as described in Example 1) two times a day for a period of 12 weeks. A follow-up after stopping the therapy was done at 4 weeks interval.

There was a marked improvement in the clinical presentation alongwith liver function tests noted at 4 weeks interval with a complete recovery occurring at the end of 8 weeks therapy with polyherbal pharmaceutical composition.

Clearance of hepatitis B virus surface antigen (HBsAg) was observed at the end of 8 weeks therapy. Anti HEV IgM disappeared after 4 weeks while anti HEV IgG persisted.

The polyherbal pharmaceutical composition therapy was stopped after 12 weeks and the liver function tests were done after 4 weeks, which were normal along with the absence of hepatitis B virus infection.

TABLE 10

Efficacy of polyherbal pharmaceutical composition in HBV Carrier with Acute HEV Super infection: shows the findings of liver function tests, hepatitis B surface antigen (HBsAg) and hepatitis E virus antibody (anti HEV IgM/IgG)

| Parameter | Initial | 4 wks | 8 wks | 12 wks | 16 wks |
| --- | --- | --- | --- | --- | --- |
| S. Bilirubin | 15.89 | 2.87 | 1.32 | 0.86 | 0.87 |
| ALT (SGPT) | 1591 | 62 | 38 | 37 | 34 |
| AST (SGOT) | 1473 | 36 | 35 | 34 | 31 |
| Alkaline Phosphatase | 267 | 124 | 129 | 122 | 105 |
| HBsAg | + | + | + | − | − |
| Anti HBc IgM | − | − | − | − | − |
| Anti HEV IgM | + | + | − | − | − |
| Anti HEV IgG | + | + | + | + | + |
| | | Therapy Period | | | Follow up period |
| | | | Therapy Stopped | | |

Normal values: AST = 10–35 IU/L; ALT = 10–40 IU/L; S. Bilirubin = 0.3–1.0 mg/dl; Alk. phosphatase = 69–170 IU/L; + = Positive; − = Negative Patient 112: A 22 year healthy female who has been a chronic carrier of hepatitis B virus (as demonstrated by the persistence of HBsAg at two different intervals of 3 months each, Anti HBc IgM=Negative, Serum Bilirubin 1.31 mg/dL, ALT=42 IU/L, AST=43 IU/L, Alkaline Phosphatase=112 IU/L, all mean values) without any clinical symptoms of a liver disease or a past history of jaundice developed acute hepatitis E virus infection (Anti HEV IgM positive) thereby presenting as acute viral hepatitis.

The Table 11 shows the details of the liver function tests at the time of presentation as acute Hepatitis (before the start of therapy) and subsequently upto 6 weeks at the interval of 2 weeks during therapy with polyherbal pharmaceutical composition.

She received the polyherbal pharmaceutical composition in the doses of two tablets (preparation as described in Example 1) two times a day for a period of 4 weeks. A follow up after stopping the therapy was done at 2 weeks interval.

There was a marked improvement in the clinical presentation alongwith liver function tests noted at the end of 2 weeks interval with a complete recovery occurring at the end of 4 weeks therapy with polyherbal pharmaceutical composition.

Clearance of hepatitis B virus surface antigen (HBsAg) was observed at the end of 2 weeks therapy. Anti HEV IgM disappeared at the end of 4 weeks while anti HEV IgG was detected at 2 weeks and persisted throughout follow-up.

The polyherbal pharmaceutical composition therapy was stopped after 4 weeks and the liver function tests were done after 2 weeks, which were normal along with the absence of hepatitis B virus infection.

TABLE 11

Efficacy of polyherbal pharmaceutical composition in HBV Carrier with Acute HEV Super infection: shows the findings of liver function tests, hepatitis B surface antigen (HBsAg) and hepatitis E virus antibody (anti HEV IgM/IgG)

| Parameter | Initial | 2 wks | 4 wks | 6 wks |
| --- | --- | --- | --- | --- |
| S. Bilirubin | 4.31 | 1.46 | 1.00 | 0.91 |
| ALT(SGPT) | 1113 | 79 | 25 | 28 |
| AST (SGOT) | 975 | 65 | 27 | 30 |
| Alkaline Phosphatase | 561 | 321 | 125 | 131 |
| HBsAg | + | + | − | − |
| Anti HBc IgM | − | − | − | − |

TABLE 11-continued

Efficacy of polyherbal pharmaceutical composition in HBV Carrier with Acute HEV Super infection: shows the findings of liver function tests, hepatitis B surface antigen (HBsAg) and hepatitis E virus antibody (anti HEV IgM/IgG)

| Parameter | Initial | 2 wks | 4 wks | 6 wks |
| --- | --- | --- | --- | --- |
| Anti HEV IgM | + | + | + | − |
| Anti HEV IgG | − | + | + | + |
| | | Therapy Period | | Follow up period |
| | | | Therapy Stopped | |

Normal values: AST = 10–35 IU/L; ALT = 10–40 IU/L;
S. Bilirubin = 0.3–1.0 mg/dl; Alk. phosphatase = 60–170 IU/L;
+ = Positive; − = Negative The above two illustrations demonstrate that the polyherbal pharmaceutical composition does not only reduce the morbidity due to superadded Hepatitis E virus infection in a healthy Hepatitis virus carrier but also helps in eliminating the underlying Hepatitis B virus infection.

Method of Treatment of Healthy Hepatitis B Virus Carriers Who Develop Super Infection with Acute Hepatitis E Virus (HEV):

The treatment relates to a super infection of Hepatitis E virus occurring in a healthy carrier of Hepatitis B virus in form of daily doses of 0.5 to 6 g of present polyherbal pharmaceutical composition in divided doses which can be administered orally daily for a period of about 3 to 6 months approximately.

HEPATITIS B VIRUS INFECTION

Screening of Pharmaceutical Preparation of *Rheum emodi* Wall. Extract in DHBV Model The Pharmaceutical preparation in the form of extract of *Rheum emodi* Wall. can be obtained by any known method and all parts or the whole of the plant *Rheum emodi* Wall. can be used to obtain extracts thereof.

The pharmaceutical preparation from the Indian plant *Rheum emodi* Wall. has been obtained and screened in DHBV model to (1) test the effects on clearance of persistent DHBV viremia, (2) prevention of the development and establishment of DHBV carrier state in non viremic ducklings, and to (3) demonstrate in vitro effects on Hepatitis B Virus (HBV). Prolonged administration of aqueous extract of *Rheum emodi* Wall. shows an encouraging response on the persistent DHBV viremia by producing DHBV clearance in 30% animals receiving therapy as well as leads to intermittent periods of non viremia in DHBV carrier ducks during treatment. Further, a prolonged administration of extract (preferably aqueous extract) of *Rheum emodi* Wall. does not produce any toxic effects on the parenchymatous organs of the animals receiving treatment. The in vitro treatment of the extract (preferably aqueous extract) of *Rheum emodi* Wall. with the infective inoculum of DHBV and its subsequent intraperitoneal administration to 72 hrs old DHBV negative ducklings inhibits the development of persistent DHBV carrier state in animals as compared to their control.

The extract (preferably aqueous extract) of *Rheum emodi* Wall. also has anti HBs and anti HBe like activity as demonstrated by in vitro effects on HBV by producing the inhibition of HBV surface antigen (HBsAg), Hepatitis B virus e antigen (HBeAg) and also has an effect on HBV-DNA.

EXAMPLE 4 describes the screening of pharmaceutical combination of *Rheum emodi* Wall. extract in Duck Hepatitis B Virus (Hepadna Virus) Model.

EXAMPLE 5 describes the in vitro effects of pharmaceutical combination of *Rheum emodi* Wall. on Hepatitis B virus (HBV).

EXAMPLE 6 describes that *Rheum emodi* does not possess any antihepatotoxic properties as demonstrated in experimental studies. Example 6 also describes that aqueous extracts of *Rheum emodi* Wall. does not produce any damage to hepatocytes at cellular level.

These examples are individually described as follows

EXAMPLE 4

This example is illustrated by experiment I and experiment II as described below:

Experiment No. I: Pharmaceutical Preparation and Elucidation of the Effects of Aqueous Extract of *Rheum emodi* Wall. on the DHBV Carrier State.

MATERIAL AND METHODS

Pharmaceutical Preparation of Aqueous Extract of *Rheum emodi* Wall.

An aqueous extract of *Rheum emodi* Wall. can be prepared by any known manner such as mixing the plant material obtained from any part of the plant with water.

Preferably, all the batches of *Rheum emodi* Wall. used in the study were collected from Sikkim, India and botanically authenticated. The roots were dried powdered and extracted with water. The extract was evaporated under reduced pressure below 50 degree celsius leaving a solid residue. The solid residue was mixed with water, kept overnight at 37° C. with stirring and supernatant was extracted by repeated centrifugation at 10,000 rpm. The solution thus obtained was vacuum dried and the dry weight of extract was determined. This dry extract was dissolved in a fixed volume of normal saline to make a stock solution and stored at 4° C. The stock solution of the extract was diluted with phosphate buffered saline (pH 7.4) to obtain the desired strength required for experimentations.

The preferred strength/quantum required for treatment can be 50 mng to 200 mg per kg/body weight and it can be administered orally daily for the stipulated period of treatment.

Production of DHBV Viremic and Non Viremic Animals for Experimentation

The Indian strain of DHBV has been characterised by cloning and sequencing (Munshi et al., 1994) and a persistent viremic/non-viremic colony of the animals were maintained. The eggs from both the groups (DHBV viremic/DHBV non viremic) were obtained, marked on shell and hatched for 30 days to obtain ducklings. The ducklings were raised on the food and water ad lib and when attaining the adulthood at age of 12 weeks were incorporated in the experiment described below.

Experimental Design: A total of 7 three month old viremic ducks were given aqueous extract of *Rheum emodi* Wall. (100 mg/kg body weight) as prepared in Materials and Methods, twice daily orally for a period of twelve (12) weeks. Post treatment follow up of the animals was carried out upto a maximum period of six (6) weeks after stopping the therapy.

Blood samples were obtained from the wing from all the ducks and stored at −70° C., after serum separation. The samples were collected prior to the start of the treatment, at weekly intervals, during the aqueous extract of *Rheum emodi* Wall. treatment and after cessation of the treatment. All the samples were subjected to determination for the presence of DHBV-DNA by Dot Blot hybridization. The animals were sacrificed at the end of their follow-up period and an autopsy was performed.

Controls: Ten ducks viremic and ten non-DHBV viremic ducks were used as controls for aqueous extract of *Rheum emodi* Wall. experiment. During the experimentation they were given normal phosphate buffer saline (placebo) in a similar protocol as with the experimental group and sacrificed with the treated animals at the end of the study.

Histopathological Studies: Liver, kidney, pancreas, heart and lungs were collected at autopsy from each animal for histopathological examination to rule out any toxic effects of the aqueous extract of *Rheum emodi* Wall. treatment. The tissue samples were fixed in buffered formalin, paraffin embedded using routine standard laboratory techniques and cut at 4 and stained with hematoxylin and eosin for examination.

RESULTS

These have been described below as (a) effect of aqueous extract of *Rheum emodi* Wall. on the persistent DHBV viremia and (b) DHBV in control group.

(a) The effects on the serum DHBV DNA during aqueous extract of *Rheum emodi* Wall. therapy and the subsequent follow up after stoppage of therapy. The results have been summarized in the table 12. Twelve weeks therapy with aqueous extract of *Rheum emodi* produced DHBV-DNA clearance in 40% animals. There were intermittent periods of DHBV-DNA clearance in 20% animals during therapy, while in 40% there was no effect.

(b) Controls: All the DHBV viremic and non viremic animals maintained their serum DHBV status during the study.

(c) Toxicity Study: Animals receiving aqueous extract of *Rheum emodi* Wall. did not reveal any significant histopathological abnormality in liver, kidney, lung, pancreas and gastrointestinal tract at the end of the study. Similarly in the control group there was no histopathological alteration in the above parenchymatous organs.

TABLE 12

Effects of therapy by aqueous extract of *Rheum emodi* Wall. on persistent DHBV infection
Duration of therapy = 12 weeks
Follow up after stoppage of therapy = 6 weeks

|  | Effect on serum DHBV DNA due to aqueous extract of *Rheum emodi* Wall. therapy | | | Control | |
|---|---|---|---|---|---|
|  | Clearance % | Intermittent effect on DHBV carrier % | No effects on DHBV carrier % | DHBV viremic | DHBV non-viremic |
| Present composition with *Rheum emodi* Wall. | 40 | 20 | 40 | 100 | — |

Experiment II: Prevention of Establishment of DHBV Viremic by Aqueous Extract of *Rheum Emodi* Wall. in Non Infected Ducklings.

Material and Methods

The pharmaceutical preparation of the aqueous extracts of *Rheum emodi* Wall. for experiment were similar to those described in Materials and Methods in experiment I.

In Vitro Treatment of DHBV with Aqueous Extract of *Rheum emodi* Wall.: 200 μL of DHBV positive serum (as detected by Dot Blot hybridization) obtained from a persistently DHBV viremic duck was mixed with 200 μL of aqueous extract of *Rheum emodi* Wall. (0.5 to 6 mg/ml preferably 4 mg/ml) and this mixture was incubated in a moist water bath at 37° C. for two hours followed by centrifugation at 2000 rpm and the supernatant was used as innoculum for ducklings (50 μl/animals) as described below.

Animals: 20 ducklings were obtained by hatching the eggs obtained from DHBV negative female ducks. The ducklings were bled immediately after hatching and serum were tested for DHBV. All the 20 ducklings were found to be negative for DHBV-DNA and were divided into following two groups:

Group A: 10 ducklings in this group were inoculated at 72 hours, with 50 μL of aqueous extract of *Rheum emodi* Wall. treated DHBV-DNA positive serum intraperitoneally.

Group B: 10 ducklings in this group were inoculated at 72 hours with 50 μL of DHBV-DNA positive and PBS treated serum intraperitoneally.

Bleeding: All the animals from Group A and B were bled at 7 days intervals post-inoculation, and upto period of 28 days and at the end of the experiments when they were sacrificed and liver, heart, kidney, lung, intestine were subjected for histopathological study.

Results: Table 13 summarises the findings of the establishment of DHBV carrier state after in vitro treatment of DHBV-DNA positive serum sample with *Rheum emodi* Wall. and its control. The percentage protection of DHBV-DNA negative ducklings inoculated with DHBV-DNA positive serum which was in vitro treated with aqueous extract of *Rheum emodi* Wall. The viremia development at the end of 28 days was only 20% as compared to the control (100%). (In other words, 80% of ducklings among the DHBV positive *Rheum emodi* Wall. treated inoculum group were protected against the development of subsequent Viremia).

TABLE 13

Shows the effects of aqueous extract of *Rheum emodi* Wall on prevention of the establishment of DHBV viremia after in vitro treatment of the inoculum

| Status of DHBV-DNA Inoculum used for Duckling | Number | Development of DHBV-DNA Viremia at weekly interval (%) | | | |
|---|---|---|---|---|---|
| | | I wk | II wk | III wk | IV wk |
| Aqueous extract of *Rheum emodi* Wall. treated (Group A) | 10 | 20 | 20 | 20 | 20 |
| Saline treated (Group B) | 10 | 100 | 100 | 100 | 100 |

On the above findings of the experiment II (when aqueous extract of *Rheum emodi* Wall. when in vitro treated with DHBV-DNA positive serum samples), the applicants presume that a sort of binding occurs with the virus thereby making latter non infectious. This observation was further extended to evaluate the effect of the duration in different hours of aqueous extract of *Rheum emodi* Wall. in vitro treatment with DHBV-DNA positive serum and the subsequent development of DHBV viremia in ducklings. The DHBV-DNA positive serum samples were treated with *Rheum emodi* Wall. extract for 1, 3 and 6 hours at 37° C. in a moist water bath and subsequently utilised as inoculum in DHBV-DNA negative duckling obtained from DHBV negative mothers as described above and followed for a period of 28 days. It was observed that the duration of aqueous extract of *Rheum emodi* Wall. in vitro treatment (hrs) with DHBV-DNA was independent of time intervals in its effects produced on DHBV infectivity and the results were similar to the two hours in in vitro treatment as described above.

EXAMPLE 5

In Vitro Effects of Pharmaceutical Combination of *Rheum emodi* Wall. on Hepatitis B Virus (HBV):

The following three sets of experiments demonstrate the presence of in vitro effects of aqueous extract of *Rheum emodi* Wall. on Hepatitis B virus surface antigen (HBsAg), Hepatitis B virus e' antigen (HBeAg) and Hepatitis B virus DNA (HBV-DNA).

a) In Vitro Effects of Aqueous Extract of *Rheum emodi* Wall. on HBsAg:

The preparation of the extract of *Rheum emodi* Wall. for the use in the experiment were similar as described in Example 1 of Experiment 1.

Clinical Material: The HBsAg positive serum samples were obtained from healthy HBV carriers (20–45 years age group), patients of acute viral hepatitis (AVH), and chronic liver diseases (Cirrhosis of liver). Each serum sample was serially two folds diluted in phosphate buffered saline and titrated for the presence of HBsAg to determine HBsAg titre. All the sera were negative for rheumatoid factor.

HBsAg Assay Method: A double sandwich solid phase enzyme immune assay (ELISA) kit using monoclonal antibody (Welcome Diagnostics, U.K.) were used to test HBsAg.

The tests were performed as per manufacturer's instructions and results were read on ELISA reader (Organon, Holland).

Treatment of Serum Samples with Aqueous Extract of *Rheum emodi* Wall.:

A 0.5–6 mg/ml, preferably 4 mg/ml concentration of *Rheum emodi* Wall. extract was used in the study. Serum samples were mixed with equal volume of *Rheum emodi* Wall. extract and incubated for 12 hours at 37° C. in a moist chamber. This mixture was centrifuged at 2000 rpm for 10 minutes and subsequently subjected to HBsAg screening by ELISA as described above. With each set of serum, controls comprising of untreated samples (saline treated) were similarly incubated for 12 hours and tested for HBsAg. The mean fall in serum HBsAg after aqueous extract of *Rheum emodi* Wall. treatment was calculated.

Results: The results of individual samples are shown in Table 14. The mean HBsAg titre of serum fell after aqueous extract of *Rheum emodi* Wall. treatment. The range of HBsAg reduction after in vitro treatment varied from 5 to 12 folds (mean 6.75).

TABLE 14

Shows the folds reduction in HBsAg titre after in vitro treatment of serum samples with aqueous extract of *Rheum emodi* Wall. in the serum samples obtained from various HBV associated conditions

| | HBsAg Serum titre | | |
|---|---|---|---|
| | Serum treated (Control) | Aqueous extract of *Rheum emodi* Wall. treated (test) | Fold reduction on HBsAg titre after aqueous extract of *Rheum emodi* Wall treatment |
| 1. Healthy HBV carrier | 1/256 | 1/16 | 5 |
| 2. Healthy HBV carrier | 1/4096 | 1/16 | 8 |
| 3. Healthy HBV carrier | 1/256 | 1/4 | 6 |
| 4. Healthy HBV carrier | 1/256 | 1/4 | 6 |
| 5. Acute HBV hepatitis | 1/64 | 1/2 | 5 |
| 6. Acute HBV hepatitis | 1/8192 | 1/2 | 12 |

TABLE 14-continued

Shows the folds reduction in HBsAg titre after in vitro treatment of serum samples with aqueous extract of *Rheum emodi* Wall. in the serum samples obtained from various HBV associated conditions

| | HBsAg Serum titre | | |
|---|---|---|---|
| | Serum treated (Control) | Aqueous extract of *Rheum emodi* Wall. treated (test) | Fold reduction on HBsAg titre after aqueous extract of *Rheum emodi* Wall treatment |
| 7. Cirrhosis liver (HBV associated) | 1/512 | 1/8 | 7 |
| 8. Cirrhosis liver (HBV associated) | 1/256 | 1/16 | 5 |
| Mean | 1/1736 | 1/8.5 | 6.75 | b) In Vitro Effects of Aqueous Extract of *Rheum emodi* Wall. on HBeAg:

The preparation of the extract of *Rheum emodi* Wall. for experiment was similar as described in experiment 1 of example 4.

Clinical Material: HBeAg positive sera were obtained from eight healthy HBV carriers, patients of Acute HBV viral hepatitis and HBV associated Liver Cirrhosis. These serum samples were serially two fold diluted in phosphate buffered saline and tested for the presence of HBeAg to determine its titre. All sera were negative for Rheumatoid factor.

HBeAg Assay Method: A double sandwich solid phase enzyme immune assay (ELISA) kit supplied by Wellcome Diagnostics, U.K. was used to determine HBeAg.

The tests were performed as per manufacturer's instructions and results were read on ELISA reader (Organon, Holland).

Treatment of Serum Samples with Aqueous Extract of *Rheum emodi* Wall.: A 0.5 to 6 mg/ml, preferably 4 mg/ml concentration of aqueous extract of *Rheum emodi* Wall. was used in the study. Serum samples serially diluted in phosphate buffered saline were mixed with equal volumes of aqueous extract of *Rheum emodi* Wall. and incubated for 12 hours at 37° C. in a moist water bath. This mixture was centrifuged at 2000 rpm for 10 minutes and subsequently subjected to HBeAg screening by ELISA as described above. With each set of samples, control comprised of untreated samples (saline treated) and similarly incubated and tested for HBeAg. The mean fall in serum HBeAg after aqueous extract of *Rheum emodi* Wall. treatment was calculated., Results: The results of the individual serum samples is shown in Table 15. The mean HBeAg titre of serum samples was 1/452.88 which fell to 1/22.80 after aqueous extract of *Rheum emodi* Wall. treatment. The range of HBeAg reduction after in vitro treatment varied from 4 to 7 folds (mean 5.25).

TABLE 15

Shows fold reduction in HBeAg titre after in vitro treatment of serum samples with aqueous extract of *Rheum emodi* Wall in the serum samples obtained from various HBV associated conditions

| | HBeAg Serum titre | | |
| --- | --- | --- | --- |
| | Serum treated (Control) | Aqueous extract of *Rheum emodi* Wall. treated (test) | Fold reduction on HBeAg titre after aqueous extract of *Rheum emodi* Wall treatment |
| 1. Healthy HBV carrier | 1/128 | 1/8 | 5 |
| 2. Healthy HBV carrier | 1/1024 | 1/64 | 5 |
| 3. Healthy HBV carrier | 1/256 | 1/18 | 5 |
| 4. Healthy HBV carrier | 1/512 | 1/8 | 7 |
| 5. Acute HBV hepatitis | 1/2048 | 1/128 | 5 |
| 6. Acute HBV hepatitis | 1/32 | 1/2 | 4 |
| 7. Cirrhosis liver (HBV associated) | 1/512 | 1/8 | 7 |
| 8. Cirrhosis liver (HBV associated) | 1/16 | 1/2 | 4 |
| Mean | 1/452.80 | 1/22.8 | 5.25 | c) In Vitro Effects of Aqueous Extract of *Rheum emodi* Wall. on HBV-DNA:

The preparation of the aqueous extract of *Rheum emodi* Wall. for experiment were similar to those described, in experiment I of example 4.

Clinical Material: Four serum samples from patients of acute viral hepatitis B positive for HBV-DNA (mean concentration 90 pg/ml) were used.

HBV-DNA Determination: A radiological molecular hybridization assay for the detection and quantitation of Hepatitis B viral DNA in serum assay (Abbott Genostics Hepatitis B Viral DNA, Abbot's diagnostics, North Chicago, USA) was used as per manufacturer's instructions to determine the HBV-DNA in serum samples both before and after in vitro treatment with aqueous extract of *Rheum emodi* Wall. The results were expressed as mean percent inhibition of HBV-DNA.

Treatment of Serum Samples with Aqueous Extract of *Rheum emodi* Wall.:

HBV-DNA positive serum samples (4) were mixed with 0.5 to 6 mg/ml preferably 5 mg/ml aqueous extract of *Rheum emodi* Wall. and incubated for 12 hrs at 37° C. in a moist chamber. Control comprised of saline treated samples and treated similarly. At the end of incubation, HBV-DNA was determined in both aqueous extract of *Rheum emodi* Wall. treated and untreated samples (controls). The results were expressed as percent inhibition of HBV-DNA concentration. Results: The mean HBV DNA of serum samples was reduced from 90 pg/ml to 28.55 pg/ml after in vitro aqueous extract of *Rheum emodi* Wall. treatment representing 31.72% reduction.

EXAMPLE 6

Experimental Hepatoprotective Studies of Pharmaceutical Combination of *Rheum emodi* Wall.

This example illustrates that the *Rheum emodi* Wall. per se does not possess anti hepatoprotective property as demonstrated by the failure to protect the liver in acute experimental hepatotoxic models. This observation is illustrated by using known acute hepatotoxic experimental models e.g. galactosamine, and paracetamol. However, *Rheum emodi* Wall. does not produce any acute toxicity in experimental animals.

The pharmaceutical preparation of the aqueous extracts of *Rheum emodi* Wall. for experiments in example 6 were similar to those described in experiment I of example 4.

Material and Methods

Animals: Adult male albino rats of body weight 125±15 g were used in the study. During the course of experiment 4 animals were kept in one cage and fed ad lib with standard pellet diet and allowed free access to water.

Histopathological Analysis: At the end of each experiment, the animals were sacrificed, their liver was removed in toto and subjected to histopathological examination.

Experiment I

Acute Paracetamol Hepatotoxicity and *Rheum emodi* Wall. Aqueous Extract

Paracetamol tablets (Calpol, 500 mg; Wellcome, India) were purchased and a dose of 2 gm/kg body weight was prepared in normal saline. Rats were administered single dose of paracetamol orally by intragastric tube. Four rats each were kept in the following four groups as follows:

Group (a): *Rheum emodi* Wall. Aqueous Extract Primed and Paracetamol Challenged Group: A twice a day dose schedule (100 mg/kg body weight) was used for the *Rheum emodi* Wall. aqueous extract treatment to paracetamol toxicated rats. In this schedule, rats were administered *Rheum emodi* Wall. aqueous extract, 48 hours prior to start of experiment and upto 7 days after receiving the single dose of Paracetamol toxication. Animals were sacrificed 7 days after the toxicant and *Rheum emodi* Wall. aqueous extract treatment.

Group (b): Saline Treated and Paracetamol Challenged Group: Four rats were given saline (500 μl) for 2 days followed by single dose of Paracetamol. Saline treatment was continued upto seven days followed by sacrifice.

Group (c): Saline Treated Group: Four rats were given saline (500 μl) twice a day and sacrificed after seven days.

Group (d): *Rheum emodi* Wall Aqueous Extract Treated Group: Four rats were given *Rheum emodi* Wall. aqueous extract 100 mg/kg body weight twice a day for seven days and sacrificed.

RESULTS

Group (a) and Group (b) Animals: The histopathological features were similar in all the animals in these two groups.

The significant histopathological alterations were presence of areas characterised by centrizonal hepatocyte necrosis of varying degree, hepatocyte degeneration with cellular inflammation (Polymorphs, mononuclear cells) focal haemorrhage, acidophilic degeneration and presence of ballooned hepatocytes.

The above findings establish that *Rheum emodi* Wall. aqueous extract does not provide any hepatoprotection activity against acute Paracetamol hepatotoxicity.

Group (c) (Saline Treated). and Aqueous Extract Treated *Rheum emodi* Wall Group (d): The histopathological features in all the animals in both the two groups were similar. The lobular architecture of liver was preserved and there was no evidence of any pathology. These findings suggest that *Rheum emodi* Wall. aqueous extract administration in rats does not lead to any damage to hepatocytes.

Experiment 2

Galactosamine Hepatotoxicity and *Rheum emodi* Wall. Aqueous Extract

Galactosamine (Sigma Chemical Company, St. Louis, USA) was used as 800 mg/kg body weight intraperitoneally as single dose. The experiment comprised of following four groups.

(a) *Rheum emodi* Wall Aqueous Extract Primed and Galactosamine Challenged Group: Four rats were given *Rheum emodi* Wall. twice a day (100 mg/kg body weight) for seven (7) days, followed by a single dose of galactosamine, alongwith one day additional *Rheum emodi* Wall. aqueous extract therapy. Animals were sacrificed twenty four (24) hours after galactosamine administration.

(b) Saline Treated and Galactosamine Challenged Group: Four rats were given saline (500 μl) twice a day for seven days followed by a single dose of galactosamine and sacrificed after twenty four (24) hours.

(c) Saline Treated Group: Four rats were given saline (500 μl) twice a day for seven days and sacrificed.

(d) *Rheum emodi* Wall. Aqueous Extract Treated Group: Four rats were given *Rheum emodi* Wall. aqueous extract 100 mg/kg twice a day for seven days and sacrificed.

Results

Group (a) and (b) Animals: The histopathological features in the liver of all the animals with or without *Rheum emodi* Wall. aqueous extract treatment and galacosamine challenge were similar.

The significant features observed were, hepatocyte balloon degeneration centrizonal hepatocyte necrosis, foamy hepatocyte vacuolation, acidophilic degeneration, mononuclear cell infiltration and occasional fatty change and portal inflammation. These findings establish that the *Rheum emodi* Wall. aqueous extract does not provide any hepatoprotection in galacosamine hepatotoxicity.

Saline Treated Group (c) and *Rheum emodi* Wall. Treated Group (d): The histopathological features of animals receiving either *Rheum emodi* Wall. or saline treatment were similar. The lobular architecture of liver was preserved and there was no evidence of any pathology.

These findings suggest that *Rheum emodi* Wall. administration in rats does not lead to any damage to hepatocytes at cellular level.

Conclusion of Hepatoprotective Studies with *Rheum emodi* Wall. Aqueous Extract:

Both the acute hepatotoxicity experiments described above demonstrate the following two features (Table 16).

a) *Rheum emodi* Wall. aqueous extract does not act as antihepatotoxic agent.

b) *Rheum emodi* Wall. aqueous extract per se does not produce any liver toxicity.

TABLE 16

Summary of Example 7

| *Rheum emodi* Wall. aqueous extract | Acute hepatotoxicity model | Hepatoprotective property |
|---|---|---|
| | Paracetamol | Absent |
| | Galactosamine | Absent |

EXAMPLE 7

Experimental Hepatoprotective Studies of Polyherbal Pharmaceutical Composition (without *Rheum emodi* Wall.)

This example describes the hepatoprotective effects of the present polyherbal preparation comprising of *Phyllanthus amarus* Linn., *Eclipta alba* Hassk., *Andrographis paniculate* Nees and *Picrorhiza kurroa* Royle ex Benth using acute hepatotoxicity experimental models. The following animal models were used:

i) Galactosamine acute Hepatotoxicity model,
ii) Thioacetamide acute hepatotoxicity model,
iii) Aflatoxin B1 acute hepatotoxicity model, and
iv) Rifampicin & Isoniazid acute hepatotoxicity model.

The details of these models are given here below:

GALACTOSAMINE (GLN) ACUTE HEPATOTOXICITY MODEL:

First reported by Keppler et al. in 1966 as a cause of hepatocellular injury GLN has been found to cause acute hepatocyte necrosis. The hepatic injury caused by GLN is an extremely interesting model and the lesion resembles that of acute viral hepatitis in humans. A single dose of GLN leads to acidophilic degeneration and necrosis of Hepatocytes in 4 to 6 hours. By 24 hours, there are multiple focal areas of necrosis often accompanied by inflammatory response of neutrophils and plasma cells. At this time the non-necrotic areas show prominent acidophilic degeneration, free acidophilic bodies, and ballooning. Enlargement and increase in number of Kupffer cells is apparent in 6 hrs and prominent by 24 hours. By 48 hours the lesion is maximal with marked dissociation of Liver cell plates and extensive areas of necrosis. Portal areas show oedema, inflammatory infiltration and bile ductular proliferation. The serum biochemical manifestation of the acute liver injury induced by GLN are characterised by an elevated serum transaminase (ALT) and alkaline phosphatase levels with or without a mild rise in serum bilirubin.

THIOACETAMIDE ACUTE HEPATOTOXICITY MODEL

Thioacetamide (Thio) is a white crystalline organic compound and a single dose (200 mg/kg) leads to centrizonal hepatocyte necrosis by 12 hours which by 24 to 30 hours is maximum and diffuse involving the complete liver lobule along with mononuclear inflammatory response.

AFLATOXIN B1 (AFB1) ACUTE HEPATOTOXICITY MODEL

Aflatoxin are a group of Furano Coumarins and at least 13 have been identified. Six of these (AFB, AFG, AFB2, AFG2, AFB20, AFGa2) are found in cultures of *A. flavus*. AFB1 is the most potent hepatotoxic and hepatocarcinogenic member of aflatoxins. Ducks are the most susceptible animal model system to study the effects of acute hepatotoxicity due to AFB1. A single dose leads to hepatocyte necrosis, fatty change, sinusoidal infiltration by mononuclear cells and proliferation of bile ductules in the portal areas.

RIFAMPICIN & ISONIAZID ACUTE HEPATOTOXICITY MODEL:

Rifampicin (RIF) is the member of rifamycin group of antibiotics with a wide spectlum activity and has achieved 'first line' status in the treatment of tuberculosis. In general, it is an agent of low toxicity, but can have pathological effects in liver. Isoniazid (INH) is also antituberculosis agent, and used in combination with RIF, INH alone can also result in liver injury, but RIF-INH combination appears to lead a higher incidence of hepatic injury than either drug alone. This is based on experimental studies that RIF and INH together are more hepatotoxic than either drug alone.

Hepatoprotective studies of the present polyherbal pharmaceutical composition (without *Rheum emodi* Wall.)were done on the duck Hepatitis B virus (DHBV) canier ducks. The following preliminary studies were done prior to detail study for Hepatoprotective effects in acute hepatotoxicity animal models.

ESTABLISHMENT OF OPTIMAL DOSES FOR ACUTE HEPATOTOXICTY MODELS

The aim of these experiments was to establish the optimal doses of each hepatotoxicant which was required to produce a damage to the liver which was compatible with the survival of the animal to study the hepatoprotective effects of the present polyherbal pharmaceutical composition without *Rheum emodi* Wall. Before the experimentation the baseline levels of serum alkaline phosphatase and ALT were determined by collecting blood samples from eight healthy DHBV viremic ducks. The serum was separated and the estimation was done using commercial kits (Bayer Diagnostics, Baroda, India) using Technicon RA50 autoanalyser as per manufacturer's instructions. The mean level of the two enzymes were as under:

|  | Meal level | Range |
|---|---|---|
| Serum Alkaline Phosphatase (IU/L) | 61 | 57–79 |
| ALT (IU/L) | 34.6 | 30–38 |

Preliminary Acute hepatotoxicity studies in both viremic and non viremic DHBV animals were carried out using Galactosamine (GLN). Thioacetamide (Thio), Aflatoxin B (AFB1), Rifamycin (RIF)+Isoniazid (INH). Blood samples were collected before and at the time of sacrificing animals for estimation of serum alkaline phosphatase and transaminase (ALT). At the end of each experiment, animals were sacrificed and liver was obtained for the histopathological study. The results established that the following optimal single doses were required to produce the desired acute hepatotoxicity in animals.

i) Galactosamine=500 mg/kg body weight ii) Thioacetamide=500 mg/kg body weight iii) Aflatoxin B1=0.1 mg/kg body weight iv) Rifamycin & Isoniazid=(250 mg RIF+150 mg INH/ combination kg body weight)

In the preliminary experiments used to standardise the above doses it was revealed that the acute hepatotoxicity produced by GLN, Thio, AFB1, REF+INH was more marked in DHBV viremic as compared to non viremic animals. Hence, only DHBV viremic animals were utilised for demonstration of hepatoprotection by present polyherbal composition.

Priming of the animals with the present polyherbal pharmaceutical composition without *Rheum emodi* Wall. was done in Galactosamine. Thioacetamide and Aflatoxin B1 toxicity models since these agents produce hepatotoxicity which is acute in nature and occurs within 48 hrs after administration of the respective toxic agent. In Rifampicin and isoniazid toxicity model, the present polyherbal pharmaceutical composition without *Rheum emodi* Wall. was administered simultaneously to the animals.

Individual hepatoprotective studies with each of the above model using the present polyherbal pharmaceutical composition without *Rheum emodi* Wall. has been described and illustrated as below:

GALACTOSAMINE ACUTE HEPATOTOXICITY MODEL

Experimental Design

1. The Present Polyherbal Composition (without *Rheum emodi* Wall.) Treated and Galactosamine Challenged Animals Six Duck hepatitis B virus (DHBV) persistently carrier adult ducks were primed with the present polyherbal composition by administering 100 mg/kg of body weight preparation orally by intragastric tube twice daily for a period of six days. On sixth day each animal received 500 mg/kg body weight galactosamine (Sigma Chemical, St. Louis, USA) as Intraperitoneal (IP) single injection. The animals were continued with the present polyherbal composition administration for 6, 7 and 8 day and were subsequently followed by sacrifice and an autopsy performed.

2. Control Group: Saline treated and galactosamine challenged animals.

Six Duck hepatitis B virus (DHBV) persistent carrier ducks were given 1 ml of normal saline orally by intragastric tube twice a day for six days. A single dose of galactosamine 600 mg/kg of body weight was given intraperitoneal (IP) injection on the sixth day. The animal received saline treatment for 6, 7 and 8 day and were followed by sacrifice and autopsy performed.

Result:

(A) Liver Histopathology

The Present Polyherbal Composition Protected and Galactosamine Challenged Animals: The hepatocytes were well preserved and arranged in well defined cell plates. The overall architecture of the liver parenchyma was normal. Photograph 17 accompanying the present specification illustrates the typical histopathological features observed in these animals.

Saline and Galactosamine Treated Animals (Control):

A marked lobular disarray of the hepatocytes was noted. There was degeneration, ballooning of the hepatocytes, along with necrosis. Foci of bile ductular proliferation were also present. Photograph 18 accompanying the present specification illustrates the histopathological features observed in these animals.

(B) Serum ALT & Alkaline Phosphatase levels in controls and the present polyherbal composition protected animals have been shown in Table No. 17

TABLE 17

Galactosamine acute hepatotoxicity model, mean values of serum alkaline phosphatase and ALT in controls and the present polyherbal composition (without *Rheum emodi* Wall.) protected animals

|  | Controls | | Protected | |
|---|---|---|---|---|
|  | Before | After | Before | After |
| Alkaline phosphatase (IU/L) | 52 | 216 | 60 | 190 |
| ALT (IU/L) | 38 | 165 | 37 | 31 |

The values represent mean of six animals.

THIOACETAMIDE EXPERIMENTAL MODEL:

The Present Polyherbal Composition (without *Rheum emodi* WalL) Protected and Thioacetamide Challenged Group:

Six Duck hepatitis B virus (DHBV) persistent canier ducks were primed with the present polyherbal composition (without *Rheum emodi*) orally by intragastric tube (100 mg/kg of body weight) twice a day for a period of six days, followed by single dose of thioacetamide (500 mg/kg of body weight intraperitoneal injection) on the sixth day. The animals were given the present composition twice a day for 7, 8 and 9 days subsequently sacrificed and an autopsy was performed.

Control: Saline Treated and Thioacetamide Challenge Animals

Six Duck hepatitis B virus (DHBV) carrier ducks were given normal saline (1 ml) for a period of six days, followed by a single dose of thioacetamide (500 mg/kg of body weight intraperitoneal injection). The animals received saline treatment on 7, 8 and 9 days subsequently sacrificed and an autopsy performed.

Results
(A) Liver Histopathology
The Present Polyherbal Composition Protected and Thioacetamide Challenged Animals The liver parenchyma was restored to normal except for the presence of fat vacuoles in the hepatocyte in some focal areas, the portal tracts were preserved. Photograph 19 accompanying the present specification clearly illustrates the histopathological features observed in these animals.

Saline Treated and Thioacetamide Challenged Animal (Control):

There was a diffuse and marked hepatocyte changes in the liver parenchyma which were characterised by necrosis, cytoplasmic degeneration and ballooning of cells. Some of the hepatocytes also showed steatosis (fatty change), Photograph 20 accompanying the present specification clearly illustrates the histopathological features observed in these animals.

(B) Serum ALT and Alkaline Phosphatase levels in controls and the present polyherbal composition protected animals have been shown in Table No. 18.

TABLE 18

Thioacetamide acute hepatotoxicity model, mean values of serum alkaline phosphatase and ALT in control and the present polyherbal composition (without *Rheum emodi* Wall) in protected animals

|  | Controls | | Protected | |
| --- | --- | --- | --- | --- |
|  | Before | After | Before | After |
| Alkaline Phosphatase (IU/L) | 60 | 182 | 79 | 92 |
| ALT (IU/L) | 34 | 137 | 32 | 34 |

The values represent mean of six animals.

AFLATOXIN B1 (AFB1) ACUTE HEPATOTOXICITY

Experimental Design

The Present Polyherbal Composition (without *Rheum emodi* Wall.) Protected and Aflatoxin B1 (AFB1) Treated Animals:

Six Duck hepatitis B virus (DHBV) persistent carrier ducks were primed with the present polyherbal composition (100 mg/kg of body weight) twice a day orally by intragastric tube for three days. On the third day, each animal received Aflatoxin B1 (Sigma Chemicals, St. Louis, USA) 0.1 mg/kg of body weight as intraperitoneal injection. The present polyherbal composition (100 mg/kg of body weight) twice a day was continued for another 6 days and the animals were sacrificed and an autopsy was performed.

Saline Treated and Aflatoxin (AFBL) Challenged Animals (control)

Six Duck hepatitis B virus (DHBV) carrier ducks received phosphate buffered saline orally by intragastric tube for 3 days followed by Aflatoxin B1 (0.1 mg/kg of body weight as intraperitoneal injection). The phosphate buffered saline treatment was continued for another 6 days and animals were sacrificed and autopsy performed.

RESULTS:
(A) Liver Histopathology
The Present Polyherbal Composition (without *Rheum emodi* Wall.) Protected and Aflatoxin (AFB1) Challenged Animals:

The lobular architecture of the liver was preserved and the hepatocytes were arranged in well defined cell plates, focal proliferation as seen in the control group was absent in the portal area. Photograph 21 accompanying the present specification clearly illustrates the histopathological features observed in these animals.

Saline Treated and Aflatoxin (AFBI) Challenged Animal (control)

There were diffuse hepatocyte changes characterised by cytoplasmic degeneration, necrosis, and ballooning of the cells. In the portal tracts proliferation of bile ductules accompanied by infiltration by mononuclear inflammatory cells was present. Photograph 22 accompanying the present specification clearly illustrates the histopathological features observed in these animals.

(B) Serum ALT & Alkaline phosphatase levels have been shown below in table No. 19.

TABLE 19

Aflatoxin B1 acute hepatotoxicity model, mean values of serum alkaline phosphatase and ALT in control and the present polyherbal pharmaceutical composition (without *Rheum emodi* Wall.) protected animals

|  | Controls | | Protected | |
| --- | --- | --- | --- | --- |
|  | Before | After | Before | After |
| Alkaline Phosphatase (IU/L) | 55 | 220 | 48 | 60 |
| ALT (IU/L) | 37 | 117 | 36 | 38 |

The values represent mean of six animals.

RIFAMPICIN & ISONIAZID ACUTE HEPATOTOXICITY

Experimental Design:
The Present Polyherbal Composition (without *Rheum emodi* Wall.) Protected and Rifampicin (RIF) and Isoniazid (INH) Treated Group:

Six Duck hepatitis B virus (DHBV) persistent carrier ducks were given the present polyherbal composition (without *Rheum emodi* Wall.) orally by intragastric tube (100 mg/kg of body weight twice a day) along with a combination of RIF 250 mg+INH 150 mg per kg body weight (Lupin Laboratories, India) daily orally for a period of seven days simultaneously, and were sacrificed at the end of study and an autopsy was performed.

Controls: Saline Treated and Rifampicin and Isoniazid Challenged

Six Duck hepatitis B virus (DHBV) persistent carrier ducks were given 1 ml of phosphatase buffered saline twice a day and RIF 250 mg+INH 10 mg per kg of body weight daily orally for a period of seven days and were sacrificed at the end of the study and an autopsy was performed.

RESULTS
(A) Liver Histopathology:
The Present Polyherbal Composition (without *Rheum emodi* Wall.) Protected and Rifampicin and Isoniazid Challenged Group:

The lobular architecture of the liver was restored to normal. The hepatocytes were arranged in well defined cell plates. Only a few hepatocytes showed fat vacuoles in their cytoplasm. Photograph 23 accompanying the present specification clearly illustrates the histopathological features observed in these animals.

Saline Treated and Rifampicin and Isoniazid Challenged Group (Control):

There was diffuse marked macrovascular type steatosis (fatty change) involving the cell cytoplasm. Photograph 24 accompanying the present specification clearly illustrates the histopathological features observed in these animals.

(B) Serum ALT and Alkaline Phosphatase levels have been shown below in Table No. 20

TABLE 20

Rifampicin and isoniazid acute hepatotoxicity model mean values of alkaline phosphatase and ALT in control and present polyherbal pharmaceutical composition (without *Rheum emodi* Wall.) protected animals

|  | Controls | | Protected | |
| --- | --- | --- | --- | --- |
|  | Before | After | Before | After |
| Alkaline Phosphatase (IU/L) | 72 | 128 | 62 | 75 |
| ALT (IU/L) | 30 | 170 | 33 | 40 |

The values represent mean of six animals.

Hepatoprotection Provided by the Present Polyherbal Composition (without *Rheum emodi* Wall.) in Acute Hepatotoxicity Experimental Models.

The four acute Hepatotoxicity experiment models described above e.g. Galactosamine, thioacetamide, Aflatoxin B1, Rifampicin and Isoniazid demonstrate that the present polyherbal composition provides a hepatoprotection which is illustrated by the liver histopathological examination and serum biochemical parameters of the liver enzymes (ALT and Alkaline phosphatase).

EXAMPLE 8

Comparison of Experimental Hepatoprotective Studies of Polyherbal Pharmaceutical Composition with or without *Rheum emodi* Wall.

Comparative Hepatoprotective Effects and Effects on Duck Hepatitis B Virus of Known Polyherbal Composition (C1) and the Present Polyherbal Composition with *Rheum emodi* (C2) and without *Rheum emodi* (C3)

A total of 80 DHBV-viremic animals were used in the study. For each acute hepatotoxicity models, the animals were primed by giving either polyherbal composition C1, C2 or C3 followed by acute hepatotoxic dose of toxicant (Galactosamine, Thioacetamide, Rifampicin+INH, and Aflatoxin B1) and subsequent administration of composition C1 or composition C2 or composition C3 twice daily. Blood samples were collected from each animal prior to the introduction in the study, during priming with either of these preparations and at subsequent intervals and at the sacrifice. Serum studies for estimation of ALT and Alkaline phosphatase were done. At the autopsy, the liver, spleen, kidney, lung and heart were removed in toto and subjected to histopathological examination.

Table 21 summarizes the comparative hepatoprotective effects of different polyherbal compositions

TABLE 21

Comparative Hepatoprotective efficacy and effects of DHBV by polyherbal compositions

|  | Polyherbal Composition | | |
| --- | --- | --- | --- |
|  | C1 | C2 (with RE) | C3 (without RE) |
| Galactosamine | +/− (very mild) | + | + |
| Thioacetamide | − | + | + |
| Rifampicin + Isoniazid | − | + | + |
| Aflatoxin B1 | − | + | + |
| DHBV | − | + | − |

RE = *Rheum emodi* Wall., DHBV = Duck Hepatitis B Virus.
+ = Present; − = Absent.

C1=Essential ingredients (extract) per dose *Phyllanthus amarus* Linn. 10–15 mg *Eclipta alba* Hassk. 15–20 mg *Andrographis paniculate* Nees. 15–20 mg. *Picrorhiza kurroa* Royle ex Benth. 10–15 mg.

C2=Essential ingredients (extract) per dose *Phyllanthus amarus* Linn. 25–250 mg *Eclipta alba* Hassk. 25–250 mg *Andrographis paniculate* Nees. 25–250 mg. *Picrorhiza kurroa* Royle ex Benth. 25–250 mg. *Rheum emodi* Wall. 25–250 mg.

C3=Essential ingredients (extract) per dose *Phyllanthus amarus* Linn. 25–250 mg *Eclipta alba* Hassk. 25–250 mg. *Andrographis paniculate* Nees. 25–250 mg. *Picrorhiza kurroa* Royle ex Benth. 25–250 mg.

EXAMPLE 9

Clinical Efficacy of Polyherbal Pharmaceutical Composition in Treatment of Acute Hepatitis B Virus Infection.

Material and Methods

Four patients (3 male, 1 female) of a mean age 31.50 (range 18–45 years) presenting within one week of the onset of their clinical symptoms suggestive of classical acute viral hepatitis (AVH) were included in the study.

The diagnosis of AVH was established by the clinical symptoms and abnormal biochemical liver function tests (Sherlock & Dooley, 1993).

The diagnosis of acute HBV infection was done on the basis of presence of HBsAg along with anti HBc IgM in the patient. The presence of other hepatitis viruses e.g. HAV (Anti HAV IgM=Negative), HCV (Anti HCV 3rd generation=Negative), HDV (Anti HDV IgM, HDAg= Negative), HEV (Anti HEV IgM=Negative), HDV (Anti HDV IgM, HDAg=Negative), HEV (Anti HEV IgM= Negative) were excluded at the initial presentation and at subsequent intervals in each patient (Sorin Diagnostics).

The other possible causes which might have lead to a similar clinical presentation e.g. surgical jaundice, drug induced cholestasis, herpes cytomegalovirus infection (as demonstrated by the absence of the respective IgM antibodies) were absent in the study patients.

In all four patients the liver function tests (Serum bilirubin, ALT) and HBsAg and anti HBc IgM (ELISA) were carried out to establish the diagnosis before the start of their therapy with Polyherbal pharmaceutical composition, and subsequently at every two week intervals during therapy upto a period of six weeks.

Prior consent of all the patients were obtained and they were explained about the treatment protocol and follow up procedure. Each patient was given 2 tablets of polyherbal pharmaceutical composition (preparation of tablets as described in Example 1) two times a day for a period of six weeks. No other therapy was given to the patients.

Results

The results demonstrating the efficacy of polyherbal pharmaceutical composition on the improvement of clinical sign and symptoms of the patients of acute Hepatitis B virus infection have been shown in table 22. The majority of clinical symptoms e.g. anorexia, loss of appetite, abdominal discomfort, lethargy and nausea etc. were relieved 2 weeks after therapy.

Table 23 summarizes the mean of biochemical test at the time of presentation and at the end of 6 week treatment with polyherbal pharmaceutical composition. Table 24, 25, 26 give detail of each liver function test parameters e.g. ALT (SGPT), AST (SGOT), Alkaline phosphatase of individual patient (No. 1 13 to 1 16) along with the mean values at the time of clinical presentation and at 2, 4 and 6 week interval during therapy with polyherbal pharmaceutical composition. A marked improvement in all the above biochemical parameters was observed at the end of 2 weeks with a complete recovery in all the 4 patients at the end of 6 weeks therapy.

Table 27 shows the presence of HBsAg and Anti HBc IgM in all the 4 patients at the time of presentation and at 2 weekly intervals during therapy with polyherbal pharmaceutical composition. All the 4 patients were HBsAg and anti HBc IgM positive at the time of their clinical presentation. At 2 weeks therapy both HBsAg and anti HBc IgM disappeared in one patient (No. 114), and Anti HBc IgM in another (No. 113). Further at the end of 4 week therapy all except one patient (No. 113) was HBsAg positive. All the four patients cleared HBV after 6 weeks of therapy with polyherbal pharmaceutical composition.

TABLE 22

Clinical efficacy of polyherbal pharmaceutical composition on physical signs and symptoms of patients of acute Hepatitis B virus infection (Number of patients 4)

| Observations | Polyherbal pharmaceutical composition therapy (Weeks) | | | |
|---|---|---|---|---|
|  | Initial | 2 | 4 | 8 |
| General well being | ++ | + | – | – |
| Anorexia | +++ | + | – | – |
| Loss of Appetite | +++ | + | + | – |
| Abdominal discomfort | +++ | ++ | + | – |
| Feeling of lethargy | +++ | ++ | + | – |
| Nausea | ++++ | + | – | – |
| Jaundice | ++++ | + | + | – |
| Hepatomegaly | ++++ | + | + | – |

+ = Mild; ++ = Moderate; +++ = Severe; ++++ = Extremely severe; – = Absent

TABLE 23

Mean levels of serum bilirubin, ALT, AST in patients of acute hepatitis B virus infection receiving polyherbal pharmaceutical composition

| No. of patients | ALT (IU/L) | | AST (IU/L) | | S. Bilirubin (mg/dl) | | Alkaline Phosphatase (IU/L) | |
|---|---|---|---|---|---|---|---|---|
|  | Initial | After Tt. | Initial | After Tt. | Initial | After Tt. | Initial | After Tt. |
| 10 | 1836.30 | 31.50 | 1472.30 | 31.00 | 5.01 | 0.86 | 388.20 | 122.90 |

Normal values:
AST = 10–35 IU/L; ALT = 10–40 IU/L;
Serum Bilirubin = 0.3–1.0 mg/dl; Alk. Phosphatase = 60–170 IU/L.

TABLE 24

Polyherbal pharmaceutical composition efficacy in acute hepatitis B virus infection shows the values of Serum Bilirubin prior to therapy and at subsequent intervals

| Patient | Polyherbal Pharmaceutical Composition Therapy | | | |
|---|---|---|---|---|
| Sl. No. | Initial | 2 weeks | 4 weeks | 6 weeks |
| 113 | 31.34 | 4.48 | 1.89 | 0.86 |
| 114 | 11.78 | 3.96 | 1.58 | 1.00 |
| 115 | 8.16 | 1.79 | 1.37 | 0.82 |
| 116 | 6.29 | 3.56 | 1.07 | 0.99 |
| Mean | 14.39 | 3.44 | 1.47 | 0.91 |

Normal Values: Serum Bilirubin = 0.3–1.0 mg/dL.

TABLE 25

Polyherbal pharmaceutical composition efficacy in Acute Hepatitis B Virus infection shows the values of Serum ALT (SGPT) prior to therapy and at subsequent interval s

| Patient | Polyherbal Pharmaceutical Composition Therapy | | | |
|---|---|---|---|---|
| Sl. No. | Initial | 2 weeks | 4 weeks | 6 weeks |
| 113 | 1453 | 95 | 39 | 36 |
| 114 | 1462 | 292 | 69 | 32 |
| 115 | 1332 | 123 | 42 | 36 |
| 116 | 2690 | 242 | 59 | 32 |
| Mean | 1734.25 | 188 | 52.25 | 34 |

Normal Values: Serum Bilirubin = 0.31–1.0 mg/dL.

TABLE 26

Polyherbal pharmaceutical composition efficacy in Acute Hepatitis B Virus infection shows the values of Serum Alkaline Phosphatase prior to therapy and at subsequent interval s

| Patient | Polyherbal Pharmaceutical Composition Therapy | | | |
|---|---|---|---|---|
| Sl. No. | Initial | 2 weeks | 4 weeks | 6 weeks |
| 113 | 254 | 179 | 128 | 118 |
| 114 | 587 | 382 | 132 | 108 |
| 115 | 239 | 169 | 128 | 120 |
| 116 | 294 | 235 | 198 | 92 |
| Mean | 343.50 | 241.25 | 146.50 | 109.50 |

Normal Values: Serum Alkaline Phosphatase = 60–170 IU/L.

TABLE 27

Polyherbal pharmaceutical composition in Acute Hepatitis B virus infection shows the status of Hepatitis B surface antigen (BBsAg) and Anti Hepatitis B Core IgM (Anti HBc IgM) prior to therapy and at subsequent interval

| Patient Sl. No. | Polyherbal Pharmaceutical Composition Therapy | | | | | | | |
|---|---|---|---|---|---|---|---|---|
|  | Initial | | 2 weeks | | 4 weeks | | 6 weeks | |
|  | HBsAg | Anti HBc IgM | HBsAg | Anti HBc IgM | HBsAg | Anti HBc IgM | HBsAg | Anti HBc IgM |
| 113 | + | + | + | + | + | – | – | – |
| 114 | + | + | + | + | – | – | – | – |
| 115 | + | + | + | – | – | – | – | – |
| 116 | + | + | – | – | – | – | – | – |

– = Negative, + = Positive

Method of Treating Hepatitis B Virus

The treatment relates to two kinds of hepatitis B virus infections namely acute (recently acquired) infection and chronic carriers (infected more than 6 months). In case of acute infection, a daily dose of 0.5 to 6 gm of the present polyherbal pharmaceutical composition can be orally administered in divided doses. Preferably, 300 mg to 1.8 g of the composition can be given orally in 2 to 4 divided doses for a period of 3 to 6 months. On the other hand, regarding chronic infection, the dosage indicated above can be given for a longer duration ranging from 6 months to 2 years.

What is claimed is:

1. A composition for treating acute hepatitis E virus infection, superadded hepatitis E virus infection in hepatitis B carriers, acute hepatitis B virus infection, animal hepadna virus infection, and chronic hepatitis B virus infection, said composition comprising extracts of plants *Rheum emodi* Wall., *Phyllanthus amarus* Linn., *Eclipta alba* Hassk., *Andrographis paniculate* Nees., and *Picrorhiza kurroa* Royle ex Benth. wherein the amount of each of the extracts of the plants *Rheum emodi* Wall., *Phyllanthus amarus* Linn., *Eclipta alba* Hassk., *Andrographis paniculate* Nees., and *Picrorhiza kurroa* Royle ex Benth, in the composition is in the range of from 25 to 250 mg.

2. The composition of claim 1 further comprising extracts of the plants *Fumaria officinalis* Linn., *Tinospora cordifolia* Miers., *Terminalia chebula* Retz., *Cichorium intybus* Linn., *Tephrosea purpurea* Linn. and *Boerhaavia diffusa* Linn. wherein the amount of each of the extracts of the plants *Fumaria officinalis* Linn., *Tinospora cordifolia* Miers., *Terminalia chebula* Retz., *Cichorium intybus* Linn., *Tephrosea purpurea* Linn. and *Boerhaavia diffusa* Linn. in the composition is in the range of from 5 to 50 mg.

3. The composition of claim 2 in the form of a tablet capsule, syrup, powder, concentrate or granule.

4. A method for treating chronic hepatitis B or hepatitis E infection, acute hepatitis E infection, superadded hepatitis E virus infection in hepatitis B carriers, acute hepatitis B virus infection, or animal hepadna virus infection comprising administering orally an effective amount of the composition of claim 2 to a patient in need thereof.

5. The compositon of claim 1 in the form of a tablet, capsule, syrup, powder, concentrate or granule.

6. A method for treating chronic hepatitis B or hepatitis E infection, acute hepatitis E infection, superadded hepatitis E virus infection in hepatitis B carriers, acute hepatitis B virus infection, or animal hepadna virus infection comprising administering orally an effective amount of the composition of claim 1 to a patient in need thereof.

7. A method for treating chronic hepatitis B or hepatitis E infection, acute hepatitis E infection, superadded hepatitis E virus infection in hepatitis B carriers, acute hepatitis B virus infection, or animal hepadna virus infection comprising administering to a patient in need thereof one or more doses of the composition of claim 1 in a day wherein the total amount of each extract of the composition administered in a day is from 250 to 1000 mg.

8. A composition in the form of a tablet wherein the composition comprises:

| Ingredients | Quantity of extracts/Tablet |
| --- | --- |
| Revand chini (*Rheum emodi Wall.*) | 170 mg |
| Bhringraj (*Eclipta alba Hassk.*) | 300 mg |
| Bhumyamalaki (*Phyllanthus amarus Linn.*) | 300 mg |
| Sarpaunkha (*Tephrosea purpurea Linn.*) | 180 mg |
| Kasni (*Cichroium intybus Linn.*) | 180 mg |
| Punarnava (*Boerhaavia diffusa Linn.*) | 100 mg |
| Gilo (*Tinospora cordifolia Miers.*) | 72 mg |
| Haritaki (*Terminalia chebual Retz.*) | 72 mg |
| Kalmegh (*Andrographis peniculate Ness.*) | 60 mg |
| Kutki (*Picrorrhiza kurroa Royle ex Benth.*) | 60 mg and |
| Pitpapra (*Furmaria officinalis Linn.*) | 30 mg, | and a pharmaceutically acceptable excipient, diluent, carrier or solvent.

9. A composition in the form of a tablet or syrup comprising:

| Ingredients | Quantity of extracts/ Tablet | Quantity of extracts for 400 Litre Syrup |
| --- | --- | --- |
| Revand chini (*Rheum emodi Wall.*) | 170 mg | 13.6 kg |
| Bhringraj (*Exlipta alba Hassk.*) | 300 mg | 24 kg |
| Bhumyamalaki (*Phyllanthus amarus Linn.*) | 300 mg | 24 kg |
| Sarpaunkha (*Tephrosea purpurea Linn.*) | 180 mg | 14.4 kg |
| Kasni (*Cichroium intybus Linn.*) | 180 mg | 14.4 kg |
| Punarnava (*Boerhaavia diffusa Linn.*) | 100 mg | 8.0 kg |
| Gilo (*Tinospora cordifolia Miers.*) | 72 mg | 5.76 kg |
| Haritaki (*Terminalia chebula Retz.*) | 72 mg | 5.76 kg |
| Kalmegh (*Andrographis paniculate Ness.*) | 60 mg | 4.8 kg |
| Kutki (*Picrorrhiza kurroa Royle ex Benth.*) | 60 mg | 4.8 kg and |
| Pitpapra (*Furmaria officinalis Linn.*) | 30 mg | 2.4 kg, | and a pharmaceutically acceptable excipient, diluent, carrier or solvent.

* * * * *